(12) United States Patent
Emery

(10) Patent No.: US 7,664,310 B2
(45) Date of Patent: *Feb. 16, 2010

(54) ADVANCED PHASE SHIFT INSPECTION METHOD

(75) Inventor: David G. Emery, Oakland, CA (US)

(73) Assignee: KLA-Tencor Corporation, San Jose, CA (US)

( * ) Notice: Subject to any disclaimer, the term of this patent is extended or adjusted under 35 U.S.C. 154(b) by 872 days.

This patent is subject to a terminal disclaimer.

(21) Appl. No.: 11/023,136

(22) Filed: Dec. 27, 2004

(65) Prior Publication Data

US 2005/0111727 A1 May 26, 2005

Related U.S. Application Data

(63) Continuation of application No. 09/991,327, filed on Nov. 9, 2001, now Pat. No. 6,836,560.

(60) Provisional application No. 60/248,149, filed on Nov. 13, 2000.

(51) Int. Cl.
G06K 9/00 (2006.01)
G01N 21/00 (2006.01)

(52) U.S. Cl. .................................... 382/145; 356/237.4

(58) Field of Classification Search ................ 382/141, 382/144, 145, 149, 224; 348/86, 125–126; 358/406, 504; 702/57, 58, 85; 356/237.4
See application file for complete search history.

(56) References Cited

U.S. PATENT DOCUMENTS 3,851,951 A 12/1974 Eveleth

| 4,247,203 A | 1/1981 | Levy |
| 4,579,455 A | 4/1986 | Levy |
| 4,633,504 A * | 12/1986 | Wihl ......................... 382/144 |
| 4,644,172 A * | 2/1987 | Sandland et al. ............ 250/548 |

(Continued)

OTHER PUBLICATIONS

Haralick, et al., "Image Analysis Using Mathematical Morphology", IEEE Transactions on Pattern Analysis and Machine Intelligence, vol. PAMI-9, No. 4, Jul. 1987, pp. 332-350.

Anil K. Jain, "Image Analysis and Computer Vision, Fundamentals of Digital Image Processing", Chapter 9, (1989), pp. 384-389.

(Continued)

Primary Examiner—Daniel G Mariam
(74) Attorney, Agent, or Firm—Smyrski Law Group, A P.C.

(57) ABSTRACT

A method and apparatus for inspecting patterned transmissive substrates, such as photomasks, for unwanted particles and features occurring on the transmissive as well as pattern defects. A transmissive substrate is illuminated by a laser through an optical system comprised of a laser scanning system, individual transmitted and reflected light collection optics and detectors collect and generate signals representative of the light transmitted and reflected by the substrate. The defect identification of the substrate is performed using only those transmitted and reflected light signals, and other signals derived from them, such as greyscale representations and image features. Defect identification is performed using a pattern inspection algorithm by comparing image feature representations of the present substrate with an idealized representation thereof, and using an advanced phase shift algorithm that accounts for particular types of expected anomalies.

20 Claims, 21 Drawing Sheets

U.S. PATENT DOCUMENTS

| | | | |
|---|---|---|---|
| 4,805,123 A | | 2/1989 | Specht |
| 4,926,489 A | * | 5/1990 | Danielson et al. ........... 382/144 |
| 5,563,702 A | * | 10/1996 | Emery et al. ................... 356/73 |
| 5,838,433 A | * | 11/1998 | Hagiwara .................... 356/364 |
| 6,148,114 A | * | 11/2000 | Han ........................... 382/256 |
| 6,282,309 B1 | * | 8/2001 | Emery ........................ 382/145 |
| 6,288,782 B1 | * | 9/2001 | Worster et al. .............. 356/394 |
| 6,836,560 B2 | | 12/2004 | Emery |

OTHER PUBLICATIONS

Masataka Shiba et al., "Automatic Inspection of Contaminates on Reticles", SPIE vol. 470 Optical Microlithography III, pp. 233-240 (1984).

James A. Freeman, et al., "Neural Networks Algorithms, Applications, and Programming Techniques, Backpropagation", Chapter 3, (1992), pp. 89-125.

* cited by examiner

FIG. 23A

|  | t1, 1 | t1, 2 | ... | t1, y−1 | t1, y | t1, y+1 | ... | t1, n−1 | t1, n |
|---|---|---|---|---|---|---|---|---|---|
|  | t2, 1 | t2, 2 | ... | t2, y−1 | t2, y | t2, y+1 | ... | t2, n−1 | t2, n |
|  | ... | ... | ... | ... | ... | ... | ... | ... | ... |
|  | tx−1, 1 | tx−1, 2 | ... | tx−1, y−1 | tx−1, y | tx−1, y+1 | ... | tx−1, n−1 | tx−1, n |
|  | tx, 1 | tx, 2 | ... | tx, y−1 | tx, y | tx, y+1 | ... | tx, n−1 | tx, n |
|  | tx+1, 1 | tx+1, 2 | ... | tx+1, y−1 | tx+1, y | yx+1, y+1 | ... | tx+1, n−1 | tx+1, n |
|  | ... | ... | ... | ... | ... | ... | ... | ... | ... |
|  | tm−1, 1 | tm−1, 2 | ... | tm−1, y−1 | tm−1, y | tm−1, y+1 | ... | tm−1, n−1 | tm−1, n |
|  | tm, 1 | tm, 2 | ... | tm, y−1 | tm, y | tm, y+1 | ... | tm, n−1 | tm, n |

FIG. 23B

|  | − | − | ... | − | − | − | ... | − | − |
|---|---|---|---|---|---|---|---|---|---|
|  | − | t2, 2 | ... | t2, y−1 | t2, y | t2, y+1 | ... | t2, n−1 | − |
|  | ... | ... | ... | ... | ... | ... | ... | ... | ... |
|  | − | tx−1, 2 | ... | tx−1, y−1 | tx−1, y | tx−1, y+1 | ... | tx−1, n−1 | − |
|  | − | tx, 2 | ... | tx, y−1 | tx, y | tx, y+1 | ... | tx, n−1 | − |
|  | − | tx+1, 2 | ... | tx+1, y−1 | tx+1, y | tx+1, y+1 | ... | tx+1, n−1 | − |
|  | ... | ... | ... | ... | ... | ... | ... | ... | ... |
|  | − | tm−1, 2 | ... | tm−1, y−1 | tm−1, y | tm−1, y+1 | ... | tm−1, n−1 | − |
|  | − | − | ... | − | − | − | ... | − | − |

ADVANCED PHASE SHIFT INSPECTION METHOD

This application is a continuation of U.S. patent application Ser. No. 09/991,327, (now U.S. Pat. No. 6,863,560) entitled "Advanced phase Shift Inspection Method," filed on Nov. 9, 2001, which is based on U.S. Provisional Patent Application 60/248,149, entitled "Advanced Phase Shift Inspection Method," filed on Nov. 13, 2000.

BACKGROUND OF THE INVENTION

1. Field of the Invention

The present invention relates generally to electro-optical inspection systems, and more particularly to a method or algorithm for automated photomask inspection to detect defects on optical masks, reticles, and the like.

2. Description of the Related Art

Integrated circuits are made by photolithographic processes which use photomasks or reticles and an associated light source to project a circuit image onto a silicon wafer. A high production yield is contingent on having defect free masks and reticles. Since it is inevitable that defects will occur in the mask, these defects have to be found and repaired prior to using the mask.

Automated mask inspection systems have existed for several years. The earliest such system, the Bell Telephone Laboratories AMIS system (John Bruning et al., "An Automated Mask Inspection System—AMIS", IEEE Transactions on Electron Devices, Vol. ED-22, No. 7 July 1971, pp 487 to 495), used a laser that scanned the mask. Subsequent systems used a linear sensor to inspect an image projected by the mask using die-to-die inspection, i.e., inspection of two adjacent dice by comparing them to each other. Other systems have been developed that teach die-to-database inspection, i.e. inspection of the reticle by comparison to the database from which the reticle was made.

As the complexity of integrated circuits has increased, so has the demand on the inspection process. Both the need for resolving smaller defects and for inspecting larger areas have resulted in much greater speed requirements, in terms of number of picture elements per second processed. The increased demands have given rise to improvements described in a number of subsequently issued patents, such as U.S. Pat. No. 4,247,203, entitled "Automatic Photomask Inspection System and Apparatus", Levy et al., issued Jan. 27, 1981; U.S. Pat. No. 4,579,455, entitled "Photomask Inspection Apparatus and Method with Improved Defect Detection" Levy et al., issued Apr. 1, 1986; U.S. Pat. No. 4,633,504, entitled "Automatic Photomask Inspection System Having Image Enhancement Means", Mark J. Wihl, issued Dec. 30, 1986; and U.S. Pat. No. 4,805,123, entitled "Automatic Photomask Inspection and Reticle Inspection Method and Apparatus Including Improved Defect Detector and Alignment Subsystem", Specht et al., issued Feb. 14, 1989. Also of relevance is some prior art in the wafer inspection area, such as U.S. Pat. No. 4,644,172, entitled "Electronic Control of an Automatic Wafer Inspection System", Sandland et al., issued Feb. 17, 1987.

Another force driving the development of improved inspection techniques is the emergence of phase shift mask technology. With this technology, it becomes possible to print finer line widths, down to 0.25 micrometers or less. This technology is described by Burn J. Lin, "Phase-Shifting and Other Challenges in Optical Mask Technology", Proceedings of the 10th Annual Symposium on Microlithography, SPIE,—the International Society of Optical Engineering, Vol. 1496, pages 54 to 79.

The above improvements teach the automatic detection of defects on conventional optical masks and reticles. In all of these systems, conventional lighting is used and the images are captured by linear array sensors. These two system choices limit the signal-to-noise ratio and hence the speed of inspection.

Additionally, photomasks are used in the semiconductor manufacturing industry for the purpose of transferring photolithographic patterns onto a substrate such as silicon, gallium arsenide, or the like during the manufacture of integrated circuits. The photomask is typically composed of a polished transparent substrate, such as a fused quartz plate, on which a thin patterned opaque layer, consisting of figures, has been deposited on one surface. The patterned opaque layer is typically chromium with a thickness of 800 to 1200 angstroms. This layer may have a light anti-reflection coating deposited on one or both surfaces of the chromium. In order to produce functioning integrated circuits at a high yield rate, the photomasks must be free of defects. A defect is defined here as any unintended modification to the intended photolithographic pattern caused during the manufacture of the photomask or as a result of the use of the photomask. Defects can be due to a variety of circumstances, including but not limited to, a portion of the opaque layer being absent from an area of the photolithographic pattern where it is intended to be present, a portion of the opaque layer being present in an area of the photolithographic pattern where it is not intended to be, chemical stains or residues from the photomask manufacturing processes which cause an unintended localized modification of the light transmission property of the photomask, particulate contaminates such as dust, resist flakes, skin flakes, erosion of the photolithographic pattern due to electrostatic discharge, artifacts in the photomask substrate such as pits, scratches, and striations, and localized light transmission errors in the substrate or opaque layer. During the manufacture of photomasks, automated inspection of the photomask is performed in order to ensure freedom from the aforementioned defects.

There are, at present, three general methods for the inspection of patterned masks or reticles. One of those inspection methods is a die-to-die comparison which uses transmitted light to compare either two adjacent dies or a die to the CAD database of that die. These comparison-type inspection systems are quite expensive because they rely on pixel-by-pixel comparison of all the dies and, by necessity, rely on highly accurate methods of alignment between the two dies used at any one time for the comparison. Apart from their high costs, this method of inspection is also unable to detect particles on opaque parts of the reticle which have the tendency to subsequently migrate to parts that are transparent and then cause a defect on the wafer. One such die-to-die comparison method of inspection is described in U.S. Pat. Nos. 4,247,203 and 4,579,455, both by Levy et al.

The second method for inspecting patterned masks is restricted to locating particulate matter on the mask. It makes use of the fact that light scatters when it strikes a particle. Unfortunately, the edges of the pattern also cause scattering and for that reason these systems are unreliable for the detection of particles smaller than one micrometer. Such systems are described in a paper entitled "Automatic. Inspection of Contaminates on Reticles" by Masataka Shiba et al., *SPIE Vol. 470 Optical Microlithography III*, pages 233-240 (1984).

A third example of a system for performing photomask inspection is disclosed in U.S. Pat. No. 5,563,702 to David G.

Emery, issued Oct. 8, 1996. The system disclosed therein acquires reflected images, in addition to transmitted images, to locate defects associated with contaminants, particles, films, or other unwanted materials. Since this system locates defects without reference or comparison to a description or image of the desired photomask pattern, it does not locate defects associated with photomask pattern errors, dislocations, or irregularities.

It has further been found to be advantageous to acquire both transmitted and reflected images for inspection of a photomask pattern with a die-to-die or die-to-database system. In particular, this approach has benefits for Embedded Phase Shift Mask (EPSM) inspection and Alternating Phase Shift Mask (APSM) inspection. Transmitted EPSM images often contain unfavorable optical characteristics due to partial coherence and interference induced by phase shifting. Some EPSM defects are simply either undetectable or indiscernible using existing die-to-die or die-to-database systems with transmitted images, but are nevertheless undesirable. Acquisition of both transmitted and reflected images for EPSM inspection has.

APSMs are typically designed with thickness variations in the glass or quartz which induce phase shift transitions between adjacent regions during photolithography. Phase defects can exist which are unwanted thickness variations created by phase etch process errors, and have similar optical image signatures during inspection. Hence APSM phase defects are difficult to distinguish from design phase features using the system shown in U.S. Pat. No. 5,563,702. Phase defects cannot be detected by this system without producing false defect readings on phase shift design features where no defects actually exist. However, the transmitted and reflected imaging capabilities and defect detection operators of this system can be useful to determine the presence of phase defects if all detected phase features are properly compared and contrasted to reference photomask image data, as in a die-to-die or die-to-database system.

Furthermore, the phase defect signal in brightfield transmitted light can be substantially less than that of a similarly sized chrome defect, thereby complicating the ability to inspect the mask. The phase defect's signal depends on a variety of factors, including the height or phase angle of the phase defect, the depth of the phase shifters, and inspection system optical parameters.

The use of reflected light in combination with transmitted light may improve detection of phase defects. The difficulty with using reflected light is managing image artifacts, such as the bright chrome halos resulting from the removal of the antireflective chrome layer during quartz etching of phase shifters. Bright chrome halos may have variable widths resulting from second write level registration tolerances with intra-plate variations. These variations are not observable when solely using transmitted light inspection techniques.

Thus, in general, phase feature signals captured with brightfield transmitted light may vary widely depending on mask and defect characteristics, and phase feature signals captured in reflected light may be stronger. On the other hand, use of reflected light can be problematic in the presence of image artifacts such as bright chrome halos. Therefore, die-to-die or die-to-database photomask inspection with transmitted and reflected light may benefit from signal-to-noise enhancements as well as an enhanced ability to discern phase shift features and phase defects.

Some references have suggested inspecting photomask substrates utilizing both transmitted and reflected light and have mentioned the possible use of both to classify defects. However, none of these references have provided details on a design using transmitted and reflected light to locate photomask pattern defects, and none have addressed the problems associated with the use of reflected light in the presence of bright chrome halos, or in the presence of particular anomalies when inspecting using brightfield transmitted light.

SUMMARY OF THE INVENTION

A preferred embodiment of the present invention includes an X-Y stage (12) for transporting a substrate (14) under test in a serpentine path in an X-Y plane, an optical system (16) including a laser (30), a transmission light detector (34), a reflected light detector (36), optical elements defining reference beam paths and illuminating beam paths between the laser, the substrate and the detectors and an acousto-optical beam scanner (40, 42) for reciprocatingly scanning the illuminating and reference beams relative to the substrate surface, and an electronic control, analysis and display system for controlling the operation of the stage and optical system and for interpreting and storing the signals output by the detectors. The apparatus can operate in a die-to-die comparison mode or a die-to-database mode.

In the present invention the speed is further enhanced by the use of a deflection apparatus previously described for laser beam recording by U.S. Pat. No. 3,851,951 to Jason H. Eveleth, entitled "High Resolution Laser Beam Recorder with Self-Focusing Acousto-Optic Scanner", issued Dec. 3, 1974.

Another advantage is the use of a stage that has only two degrees of freedom. Prior systems incorporated rotational capability at a considerable cost and complexity. In the present invention the effective direction of scanning is controlled by driving both axes of the stage simultaneously.

The present system also has the ability to simultaneously detect defects with both transmitted and reflected light. This capability is significant because the additional information can be helpful in determining the nature of the defect and thereby permits the automatic classification of defects.

Yet another advantage of the first aspect of the present invention is its ability to inspect phase shift masks. Phase shift mask technology may be used to achieve line widths of 0.10 micrometers. In the present invention the phase shift material can be measured at all points on a mask area at the normal scanning speed of the system.

In accordance with the present invention there is provided a novel method and apparatus for the inspection of photomasks at a high sensitivity to detect submicron particulate contamination, chemical stains and residues, and localized transmission variations by utilizing synchronized transmitted and reflected light signals (i.e. from the same location on the substrate with either the same light beam or two light beams of equal intensity and cross sectional size and shape illuminating the same location on the substrate).

Further there is provided a pattern inspection algorithm on both the transmitted and reflected images to determine defects at and around the edges of the specimen pattern. The system simultaneously samples transmitted and reflected images and passes the data to a remapping block which converts each T-R image sample to a single output greyscale value. The remap function is designed to produce images with corrected optical characteristics by reference to reflected greyscale data, which is not altered by transmissive phase-shifting. The system performs a pattern inspection algorithm on the remapped image to determine defects at and around the specimen pattern. By remapping the transmitted and reflected images into a single image, the processing requirements for preprocessing, alignment, interpolation, and comparison need not be duplicated for both images. The remap correction requires an analysis of the correlated relationships between transmitted and reflected greyscale values.

The remap function is determined before inspection during a calibration procedure by evaluating samples of representative transmitted and reflected images. The calibration can be performed by various methods, where the common objective is to analyze the correlation between transmitted and reflected values and assign an appropriate relationship between transmitted and reflected input values and remap output values. For any method, remap calibration must function effectively in the presence of greyscale measurement noise.

To allow for noise, off-curve points may be parameterized by selecting the nearest neighbor on the curve. After the entire TR-plane is completely parameterized, the remap function is then stored into the remapping block for reference during inspection.

Subsequent to the initial calibration procedure, the system scans the desired specimen to inspect it for defects. The system remaps the TR readings into single greyscale values thereby permitting a combination of transmitted and reflected images into a single intensity profile. The system may include filters networks to improve detectability.

The remapped optical image is further processed in a transform block in preparation for alignment and comparison with a pattern reference image. If the reference image is derived from a database, the database image is also processed in a transform block. Data from both the optical transform block and the database transform block are provided to the align, interpolate, and compare block which evaluates the distance code values from the database and from the scanned specimen and determines differences between the values.

One aspect of the present invention is based upon a laser scanner, optical conditioning subsystem, a stage, reflectance and transmission detectors, and an autofocus subsystem as disclosed in the above cross-referenced Wihl patent application.

The system further includes a transmitted and reflected light algorithm or method for improving detection of particular types of features expected to be encountered on the mask. The algorithm provides the system with the ability to differentiate and resolve anomalies found on strong phase shift type masks, including alternating and darkfield alternating phase shift mask types. Further, the algorithm provides the ability to manage image artifacts such as bright chrome halos. The algorithm determines the remap function S=S(T,R), utilizing different species employing different analytical approaches to derive the remap. The species are each designed for a specific anticipated application, and thus the algorithm operates as an expert system to locate anticipated anomalies.

These and other objects and advantages of all of the aspects of the present invention will become apparent to those skilled in the art after having read the following detailed disclosure of the preferred embodiments illustrated in the following drawings.

DESCRIPTION OF THE DRAWINGS

FIG. 23a is a pixelized transmission image of the substrate being inspected.

FIG. 23b is a pixelized second derivative transmission image, derived from the pixelized transmission image of the substrate being inspected.

DETAILED DESCRIPTION OF THE INVENTION

Figure 1:
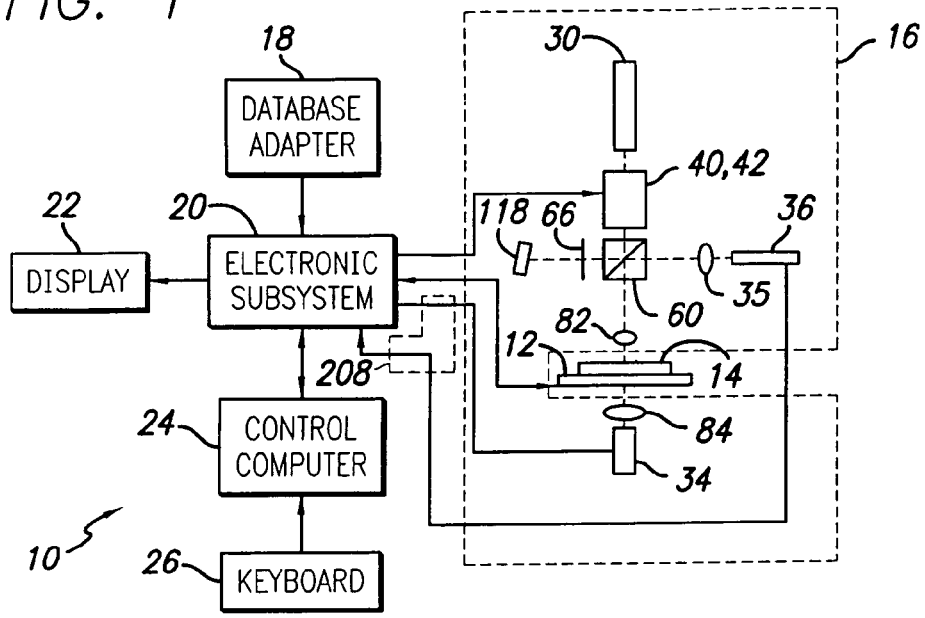
FIG. 1 is a simplified functional block diagram of a laser mask inspection system in accordance with the first aspect of the present invention.

Referring now to the drawings, a block diagram of an automatic optical inspection system in accordance with the first aspect of the system is shown at 10. The system is capable of inspecting substrates, such as reticles, photomasks, semiconductor wafers, phase shift masks, and Embedded Phase Shift Masks (EPSMs).

The system can perform several types of inspection: transmitted light inspection, reflected light inspection, simultaneous reflected and transmitted inspection, and phase shift measurement. In transmitted light inspection, light impinges on the substrate, a photomask for example, and the amount of light transmitted through the mask is detected. In reflected light inspection, the light reflecting from a surface of the substrate under test is measured. During phase shift inspection, the amount of phase shift between two reflected coherent light beams is detected at each point on the mask while transmitted light inspection takes place concurrently. The phase shift is proportional to the relative elevation of the surface from which the beams are reflected. As will be explained below, the transmitted light signal is used to qualify the phase-shift signal. In addition to these defect detection operations, the system is also capable of performing line width measurement.

In all of the defect detection operations a comparison is made between two images. In die-to-die inspection mode two areas of the substrate having identical features (dice) are compared with respect to each other and any substantial discrepancy is flagged as a defect. In the die-to-database inspection mode a defect is detected by comparing the die under test with corresponding graphics information obtained from the CADS (computer aided database system) database from which the die was derived. In the latter case the CADS database is converted to an image format as explained in U.S. Pat. No. 4,926,489. (Danielson at al., "Reticle Inspection System", issued May 15, 1990).

As depicted in the simplified block diagram of FIG. 1, a preferred embodiment of the system 10 includes a stage 12 for carrying a substrate 14 to be inspected, an optical subsystem 16, a data base adaptor 18, an electronics subsystem 20, a display 22, a control computer 24 and a keyboard 26.

The Stage

Although a preferred embodiment of the stage 12 will be described in detail below, it suffices at this point to say that the stage is a precision device driver under control of subsystem 20 and is capable of moving the substrate 12 under test in a serpentine fashion, within a single plane, relative to the optical axes of the optical subsystem 16 so that all or any selected part of the substrate surface may be inspected.

Optical Subsystem

Figure 2:
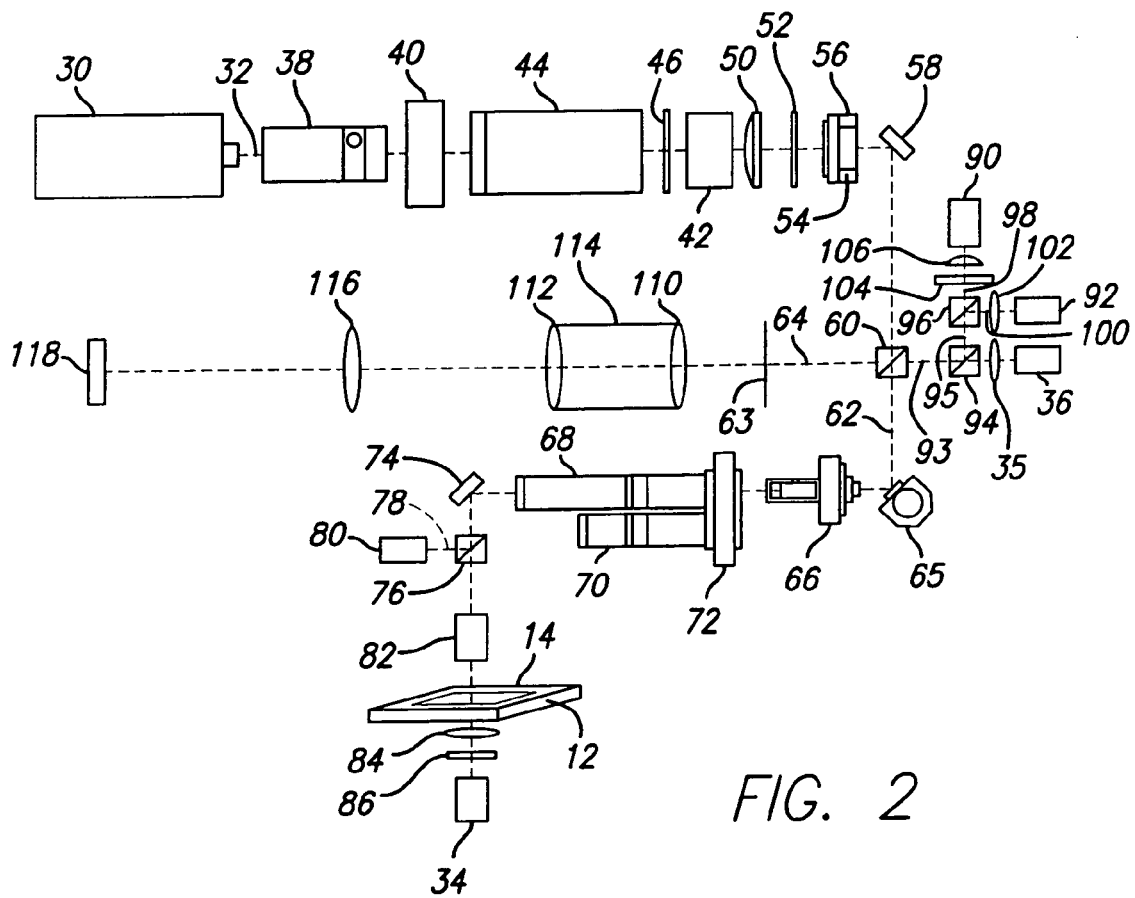
FIG. 2 is a more detailed schematic representation of the optical subsystem depicted in FIG. 1.
Figure 3:
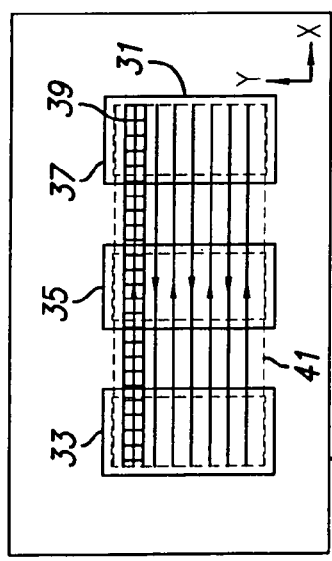
FIG. 3 is a diagram illustrating the scanning path used in the die-to-die inspection mode.
Figure 4:
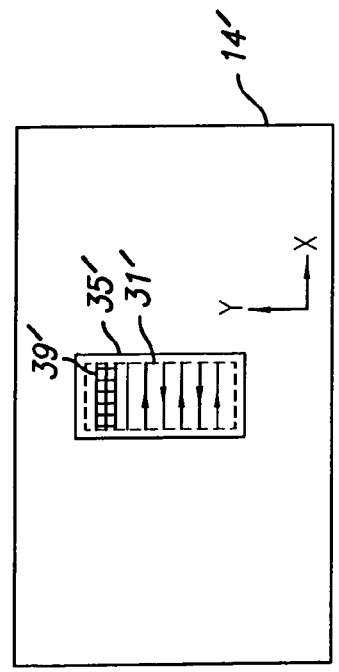
FIG. 4 is a diagram illustrating the scanning path used in die-to-database inspection mode.

A detailed block diagram of the optical subsystem 16 is shown in FIG. 2 and is essentially a laser scanner apparatus including a light source 302 and associated optics which cause a beam 32 of coherent light to be deflected over a small angle, i.e., from one side to the opposite side of the optical axis defined by the optical subsystem 16. As will be further described below, the beam sweep is in a direction such that, after passing through the optical system, it is directed parallel to the Y-axis as viewed at the substrate 14. As the beam is swept, the stage 12 carrying the substrate 14 under test is caused to move back and forth in the direction of the X-axis, being incremented in the Y-direction at the end of each traverse so that the beam 32 is caused to sweep along a serpentine path 31 across a plurality of identified substrate subareas 33, 35, 37 (individual dice in the case of a photomask) as indicated in FIGS. 3 and 4. In this manner the entire surface area of the substrate (mask) 14 is swept in a series of contiguous swaths 39 by the laser beam. In the case of a transparent or partially transparent substrate, detection of the image is accomplished by a transmission detector 34. In the case of a reflective or partially reflective substrate, the light reflected from the substrate is detected by a reflected light detector 36. As will be explained in more detail later, phase shift mask inspection is carried out by using both of these detectors simultaneously.

The light source 30 of the system is a laser, such as the Model 5490A5L-00C-115 made by Ion Laser Technology of Salt Lake City, Utah. The light beam 32, emitted by the laser 30, first passes through a spatial filter 38 and is then deflected by the combination of two acousto optic elements; an acousto-optic prescanner 40 and an acousto-optic scanner 42. These two elements deflect the light beam in the Y-direction and focus it in the X-direction in a manner similar to that described in U.S. Pat. No. 3,851,951. (Jason H. Eveleth, "High Resolution Laser Beam Recorder with Self-focusing Acousto-optic Scanner", issued Dec. 3, 1974). The deflection system also includes a beam expander 44 and a quarter wave plate 46.

When the beam emerges from the scanner 42, it is convergent in the Y-direction, but collimated in the X-direction. A cylindrical lens 50 then also focuses the beam in the X-direction, with the focal plane for both X and Y axes lying at a field stop 52. The beam next passes through a quarter wave plate 54 and a relay lens 56.

The beam is then reflected by a mirror 58, the sole function of which is to fold the optical path. The redirected beam then enters a cube beam splitter 60 which divides it into paths 62 and 64. The latter path is used only in the phase measurement mode and is otherwise blocked by a shutter 63.

The beam continuing along path 62 is reflected by an oscillating mirror 65 which is held fixed during the inspection operation and is used only for displaying an image to an operator on an image display (not shown in FIG. 2) during alignment and review. A dove prism 66 is used to rotate the direction of the scan about the optical axis. The output of prism 66 is fed to one of the telescopes 68 and 70 mounted on a rotatable turret 72. The purpose of these telescopes is to vary the size of the scanning spot on the substrate 14 and thereby allow selection of the minimum detectable defect size. Since changing the magnification also varies the length of the scan, the swath width is also changed and therefore the inspection speed. (Only two telescopes are shown but obviously any number of telescopes, and therefore spot sizes, can be used.)

From the telescope the beam passes to a mirror 74 and then to a beam splitter 76 where the path is again split. The reflected portion of beam 78 is directed to a detector 80 which serves as a monitor of the beam intensity variation. The unreflected portion of the beam passes through an objective lens 82 which focuses the beam onto the substrate 14. Light passing through the substrate 14 is then collected by a condenser lens 84 and a collector lens 86, and focused onto the transmission detector 34.

Autofocus Subsystem

The autofocus function is based upon a monitoring of the shape of the light beam cross-section after it is passed through some anamorphic elements. The basic principle underlying the implementation is that a cylindrical lens produces astigmatism. In such a case a focussed beam first passes through best focus in one direction and then through best focus in the perpendicular direction. In between these two focal points along the beam path the beam cross section is oblong in one direction and transitions along the path through points where the beam cross section is circular and then oblong in a direction perpendicular to the previous direction. In this invention the optimum focus of the light impinging on the substrate is detected by monitoring the beam cross section of light reflected from the substrate 14. The shape of the beam cross section is monitored by two silicon quadrature photodiodes 90 and 92, such as made by Silicon Detector Corporation of Newbury Park, Calif.

As is explained in more detail below, the actual autofocus system consists of two optical paths which differ from each other in the direction of the astigmation. In one path the cylindrical lens has no curvature when viewed in the X-direction while in the other path, the cylindrical lens has no curvature in the Y-direction.

Figure 5:
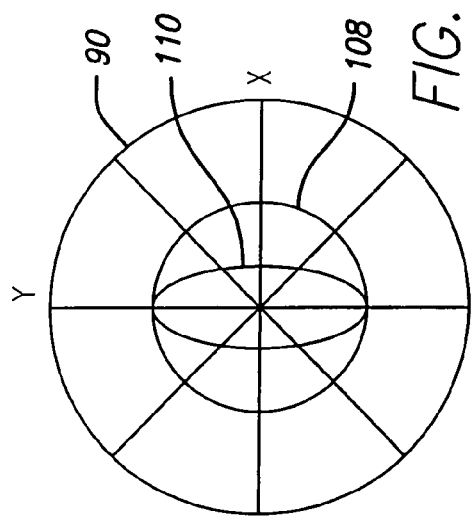
FIGS. 5 and 6 are diagrams illustrating possible beam cross sections used in the autofocus system.
Figure 6:
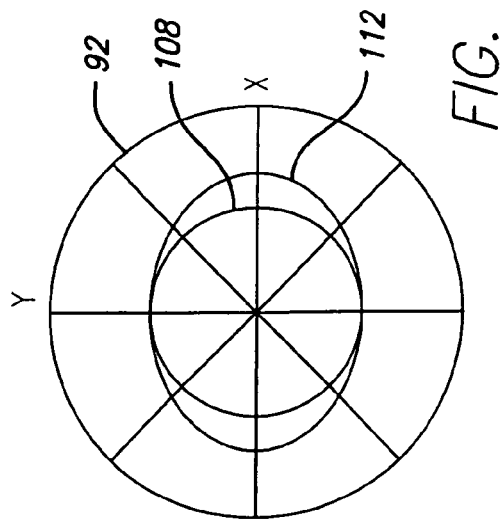

The autofocus beam 93 is split off from the reflected beam 95 directed along reflected detector path by a beam splitter 94, and is redirected toward another beam splitter 96 which splits the beam into two paths 98 and 100. In FIG. 2 the x-coordinate is perpendicular to the paper and consequently, cylindrical lens 102 is shown with a curvature, while an identical element 104, in the other path, appears as a plano-parallel element. The path leading to detector 90 also contains a spherical lens, 106. The two identical quadrature detectors 90 and 92 detect a cross-section of each beam. As the substrate surface position, or thickness, varies, the beam cross section, as seen by the detectors, varies in the X-direction as shown in FIGS. 5 and 6 at 108, 110 and 108, 112 respectively. On neither detector does the vertical (Y-direction) diameter of the illuminated area change. When the mask is in focus, both detectors are illuminated by a circular beam 108. As the mask goes out of focus, the horizontal diameter shrinks on one detector (see FIG. 5), while on the other one it increases (see FIG. 6) as indicated by the outlines of the beam 110 and 112, respectively. This changes the electrical output from the quadrature detectors. The focus correction signal $F_c$ is then:

$$F_c = \frac{(A_1 - B_1) - (A_2 - B_2)}{(A_1 + B_1) + (A_2 + B_2)}$$

where $A_1$ is the signal derived from quadrants along the X axis of 90, $A_2$ is the signal derived from quadrants along the X axis of 92, $B_1$ is the signal derived from quadrants along the Y axis of 90, $B_2$ is the signal derived from quadrants along the Y axis of 92.

Transmitted Light Inspection Mode

Ordinarily, transmission mode detection is used for defect detection on substrates such as conventional optical masks having transparent areas and opaque areas. As the laser beam scans the mask, the light penetrates the mask at transparent points and is detected by transmitted light detector 34 which is located behind the mask 14 and measures the light collected by condenser lens 84 and collector lens 86.

Reflected Light Inspection Mode

Reflected light inspection is normally performed on opaque substrates that contain image information in the form of developed photoresist features. Light reflected by the substrate passes backwards along the same optical path as described before but is then diverted by a polarizing beam splitter 60 into detector 36. A condenser lens 35 projects the light onto the detector 36. As previously stated, during reflected light inspection, shutter 63 is closed.

Reflected light inspection may also be used to detect contamination on top of opaque substrate surfaces.

Phase Shift Material Thickness Measurement Mode

The measurement of phase shift is of interest only at points where the substrate is transparent, i.e., where there is no opaque geometry. The presence of opaque geometry is detected by the transmission detector 34 and only in the spaces separating such geometry is a phase shift measurement taken. During this operation shutter 63 is open and light from the laser reflected by splitter 60 travels through relay lenses 110 and 112, which form a telescope 114, and through a low numerical aperture objective lens 116 to a tilted mirror 118 where it is reflected by detector 36. At the same time, detector 36 is also illuminated by light which first passes through splitter 60 to be reflected from a point on the substrate and which on returning is reflected by splitter 60 to the detector. These two luminous beams interfere with each other, and the intensity of the light detected by detector 36 therefore varies as a function of the relative optical path length of the two paths 62 and 64. As will be explained in more detail later, this data is interpreted by the electronic subsystem to determine variations of thickness of phase shift material covering a given point on the substrate.

Simultaneous Detection by More than One Type of Detector

Transmitted and reflected light inspections and the phase shift measurement operation are not mutually exclusive in time. Simultaneous transmitted and reflected detection can disclose the existence of an opaque defect sensed by the transmitted detector while the output of the reflected detector can be used to disclose the type of defect. As an example, either a chrome dot or a particle is opaque and hence will result in a dark output from the transmission detector, but reflective chrome defects also produce a high reflected light indication while a particle will typically reflect less. By using both reflected and transmitted detection one may locate a particle on top of chrome geometry. In general, one may determine signatures for certain types of defects, such as the ratio of their reflected and transmitted light intensities. This information can then be used to automatically classify defects.

Similarly, transmitted light detection and phase shift measurement can occur simultaneously. On a phase shift mask an opaque defect in a region covered by phase-shift material can be detected, and the absence of opaque material detected by the transmitted light detector 34 can be used to gate the phase shift measurement.

Control Computer

The control computer 24 acts as the operator console and master controller of the system and is a device such as a SPARC computer made by Sun Microsystems of Mountain View, Calif. All system interfaces with the operator and the user's facilities are made through the control computer. Commands are issued to and status is monitored from all other subsystems so as to facilitate completion of the operator assigned tasks.

Electronics Subsystem

The function of the electronics subsystem 20 is to interpret and execute the commands issued by control computer 24. These functions are: digitize the input from detectors 34 and 36; compensate these readings for variations in the incident light intensity; detect defects in the image and transfer the defect data to the control computer 24; accumulate the output of the interferometers used to track the stage 12; provide the drive for the stages linear motors; and monitor sensors which indicate status.

Except for the measurement of phase shift and line width information, all of the enumerated functions of control computer 24 and subsystem 20 have been described in U.S. Pat. Nos. 4,247,203, 4,579,455, 4,633,504, 4,805,123, 4,926,489, and 4,644,172. In the above patents the same functions are performed in many different ways and the particular approach adopted depended on the availability and suitability of integrated circuit devices at the time the system was being developed. Any of the cited approaches could be used.

The Stage

The stage 18 is an air-bearing X-Y stage that is driven by a linear motor on each axis. The position of the stage along each axis is monitored by interferometers (not shown), such as the Model TIPS V, made by Teletrac Corporation.

Figure 7:
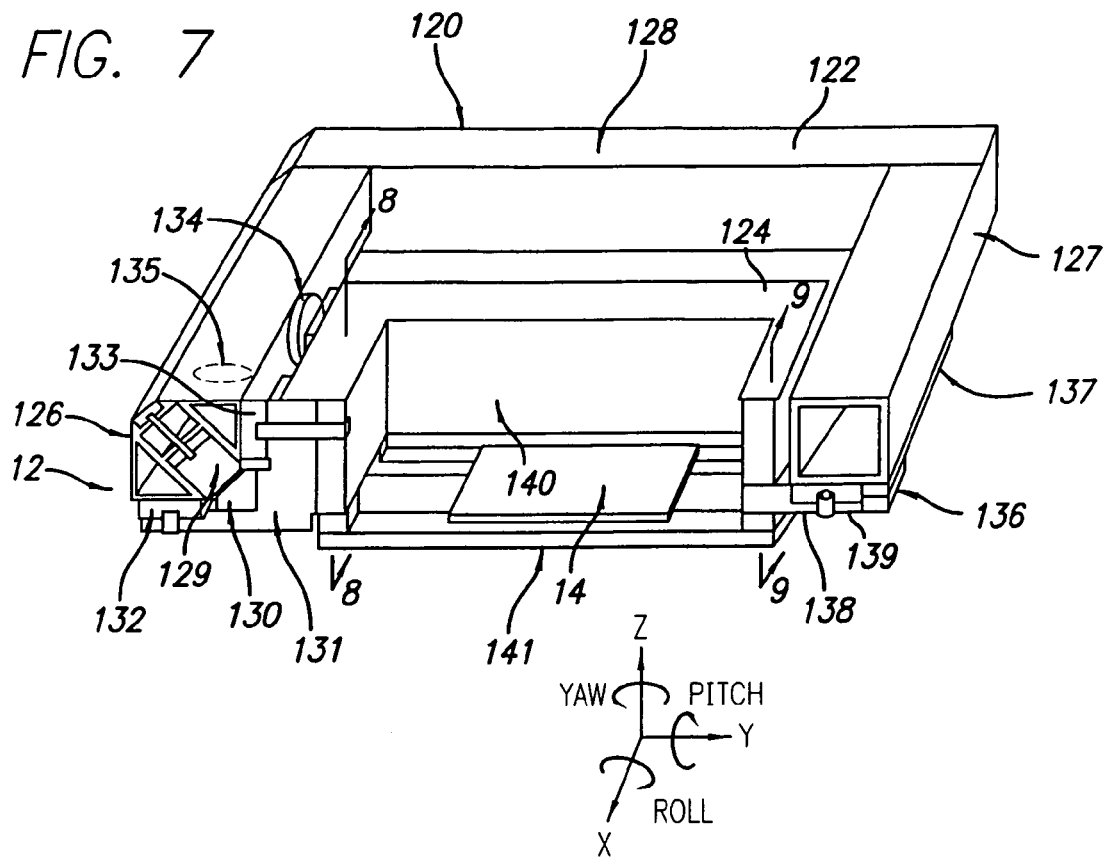
FIG. 7 is a partially broken perspective drawing illustrating the X-Y stage.

Stage 18 is shown in detail in FIG. 7 with the front rail cut away to permit view of the principle elements. The stage has two degrees of freedom; it has no rotational capability. It is disclosed here for application in the described inspection system but could also be used in microlithography and any precision machining application.

The Y carriage 120, in the shape of a frame 122, carries the X stage 124. The motion of both stages is controlled by linear motors and air bearings. The attractive force between the stator and the slider of each linear motor provides the preload of the linear bearings.

The Y carriage frame includes two guideways 126 and 127, controlling the motion of the X stage 124 inside the carriage. The guideways are connected by two side rails 128. (The front rail, the equivalent of 128, is not shown.) The stator 129 of the X linear motor is imbedded inside the X guideway 126 in such a way that it attracts the X slider 130 attached to air-bearing housings 131 and preloads four of the five X air bearings 132, 133, 134 and 135. A separate magnet 136 and ferromagnetic preload strip 137 provide the preload to air bearing 138. Each bearing is equipped with a swivel, enabling rotation of the bearing pad about two axes, in addition to rotating the bearing itself, thus the only degree of freedom constrained by an air bearing is the translation in the direction normal to the pad surface.

The X stage carries the specimen 14 and is kinematically constrained by the five air bearings: the bearings 132 and 135 control the pitch of the X stage motion, and constrain the vertical translation in the Z direction, bearings 133 and 134 control the yaw of the X motion and constrain the horizontal translation in the Y direction. Bearing 138 nested in the housing 139 controls the roll of the X stage and constrains vertical translation of the stage in the Z direction. The specimen holder assembly 140 is attached to a lightweight composite frame 141 of the X stage.

The stage contains a number of novel features. One such feature is the use of the linear motor to preload the stage in two directions and thereby achieve an exceptional stiffness. This is accomplished by the arrangement of triangular cross section slider iron 130 and angular position of the stator 131, so that the magnetic attraction force is at an angle to all four air bearings 132, 133, 134 and 135.

Another feature of the design is that the stator 129 of linear motor is imbedded inside the guideway 126 at an angle to the two walls of the guideway.

Figure 8:
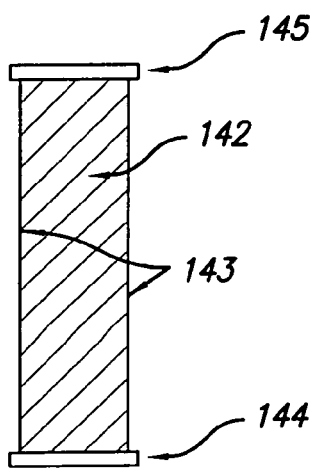
FIG. 8 is a cross-section taken along the line 8-8 of FIG. 7 showing details of the construction frame of the stage.

Also novel is the use of honeycomb material, such as Blue Seal, made by Hexcell of Dublin, Calif., for the construction of frame 140. This reduces the mass of the stage, yet makes it very rigid. A cross-section of this construction taken along the line 8-8 is shown in FIG. 8 where cellular insert 142 is sandwiched between skins 143. The bottom plate 144 and top plate 145 join the skins 143 and complete the box structure enclosing the insert 142. The honeycomb material may be replaced by any number of light composite materials, such as Duocell, manufactured by ERG of Oakland, Calif.

Figure 9:
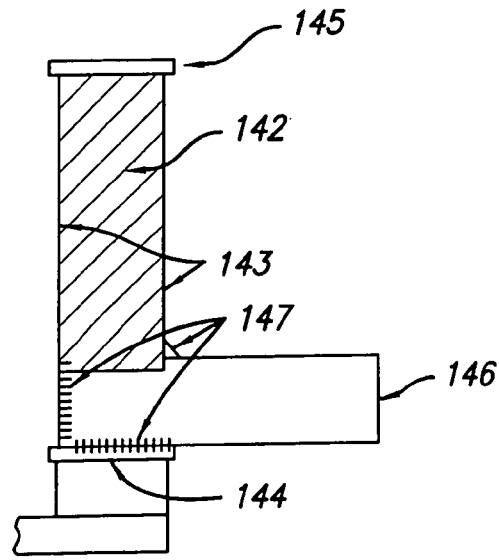
FIG. 9 is a cross-section taken along the line 9-9 of FIG. 7 showing other details of the construction frame of the stage.

Solid pieces 146 are attached to the composite such that they penetrate one skin of the composite wall and are attached to the opposite skin and either of the top or bottom plates, as shown in FIG. 9, with joints 147 formed around the penetration through the wall, and between the solid piece and the inside of the opposite skin and the plate 144.

Operation of the Disclosed Embodiment Alignment

Prior to starting the automatic inspection operation, the operator aligns the mask in the proper orientation and defines to the computer the "care area", i.e., the area to be inspected. FIG. 3 illustrates the desired orientation of the inspection path 31 with respect to dice 33, 35, and 37 shown here on a multi-die mask or reticle 14. During inspection, the stage 12 is moved in a serpentine manner, following the path 31, while the laser beam is deflected parallel to the Y-axis of the mask. As stage 12 moves in the X-direction, this Y-axis motion of the laser beam sweeps out a swath, 39. Ordinarily the axes of mask 14 will not be parallel to the drive axis of the stage. Therefore, an X or a Y directional motion of the stage requires both of the drives of the stage to be driven simultaneously. The first task of the operator is therefore to define to the system the ratio of the speeds of the major axes of the stage. To accomplish this, the operator chooses two points known to him to lie on the same X-coordinate of the die. He then drives the stage to these points, while observing the image on image display 22. The system notes the location of these points by measuring the travel with interferometers (not shown) along the drive axes of the stage. These measurements establish the direction cosines of the stage drive axes with respect to the X and Y axes of the mask. At this time the dove prism 66 (FIG. 2) is rotated to orient the deflection of the laser beam so that it is perpendicular to the X-directional travel of the stage. Next, the operator designates to the system the care area 41 (FIG. 3) of the die, the area to be inspected.

Phase Shift Measurement Calibration

Figure 11:
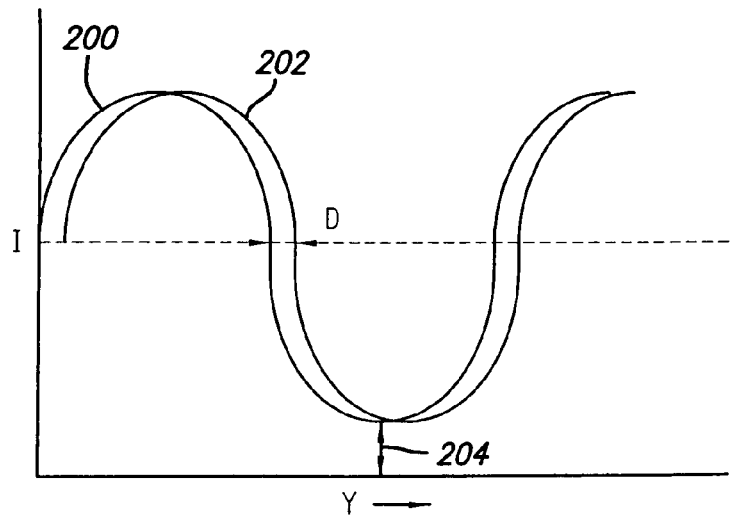
FIG. 11 is an illustration of the sinusoidally varying detected signal intensity as the mask is scanned in phase shift measurement mode.

For reasons that will become apparent later, in the phase measurement mode, as the laser spot scans (in the Y-direction), a flat transparent surface parallel to the plane of the mask, the intensity varies sinusoidally, as shown by curve 200 in FIG. 11. Mathematically, the intensity I is:

$$I = A \sin[(2\pi y/w) - D] + I_o.$$

where y is the distance of the pixel in question from the origin, w is a constant that is a function of the tilt angle of mirror 118, D is the phase shift due to path length change as the result of the thickness of the phase shift material, A is the half-amplitude of the intensity, and $I_o$ is the intensity offset 204 due to stray light in the optics. These values are all determined during the phase shift measurement calibration part of the initialization. As the laser scans a flat uniform transparent area of the mask, the intensities at each picture element (pixel) are digitized and stored in the computer. Then, $I_o$ is the average value of the intensities over integer cycles, and A can be computed from:

$$A = (I_{max} - I_o)/2$$

The value W is the periodicity of the sinusoid.

$I_o$ and A are different for clear and phase shift material covered areas and therefore must be determined for both areas. The quantity D is a linear function of the thickness of the phase shift material and this relationship is determined by calibration on a known sample containing various thickness phase shift material features and remains constant while the system retains dimensional stability.

The Inspection Process

Automatic inspection of a reticle ordinarily starts at the upper left hand corner of the care area and follows the serpentine pattern 31 (see FIG. 3). As the stage slowly moves in the X direction, the laser beam rapidly sweeps in the Y-direction. In this manner a swath 39 is scanned and the digitized output of the detectors is stored in the electronics subsystem 20. When the swath reaches the left boundary of the care area of the second die 35, image data derived from die 33, and now stored in subsystem 20, is compared with the data derived from die 35. Any substantial difference is designated a defect. In a similar manner, the data from die 37 is also compared with the data derived from die 35.

When the scanning process reaches the right boundary of the care area of die 37, the stage is moved in the Y-direction an amount slightly less than the swath width and the stage starts a return trace in the X-direction. In this manner the care areas of the dice are traversed by the serpentine motion.

Die-to-database inspection, ordinarily performed on single die reticles, is similar to die-to-die inspection except that the comparison occurs between the die and a simulated image generated by database adaptor 18. FIG. 4 illustrates the die-to-database scan path 31'.

Review Operation

After completion of the automatic inspection operations, the operator reviews the defects by causing control computer 24 to move the stage 12 to the area of a particular defect and hold it there. The image is then scanned by acousto-optic scanners 40 and 42 in the Y-direction and by oscillating mirror 65 in the X-direction, and the digitized image is displayed on display 22. The operator may use the output of any of the detectors or the combination of outputs from more than one detector. If the operator desires, the different detector outputs may be superimposed and represented as separate colors on the display.

Phase Shift Material Thickness Measurement

Figure 10:
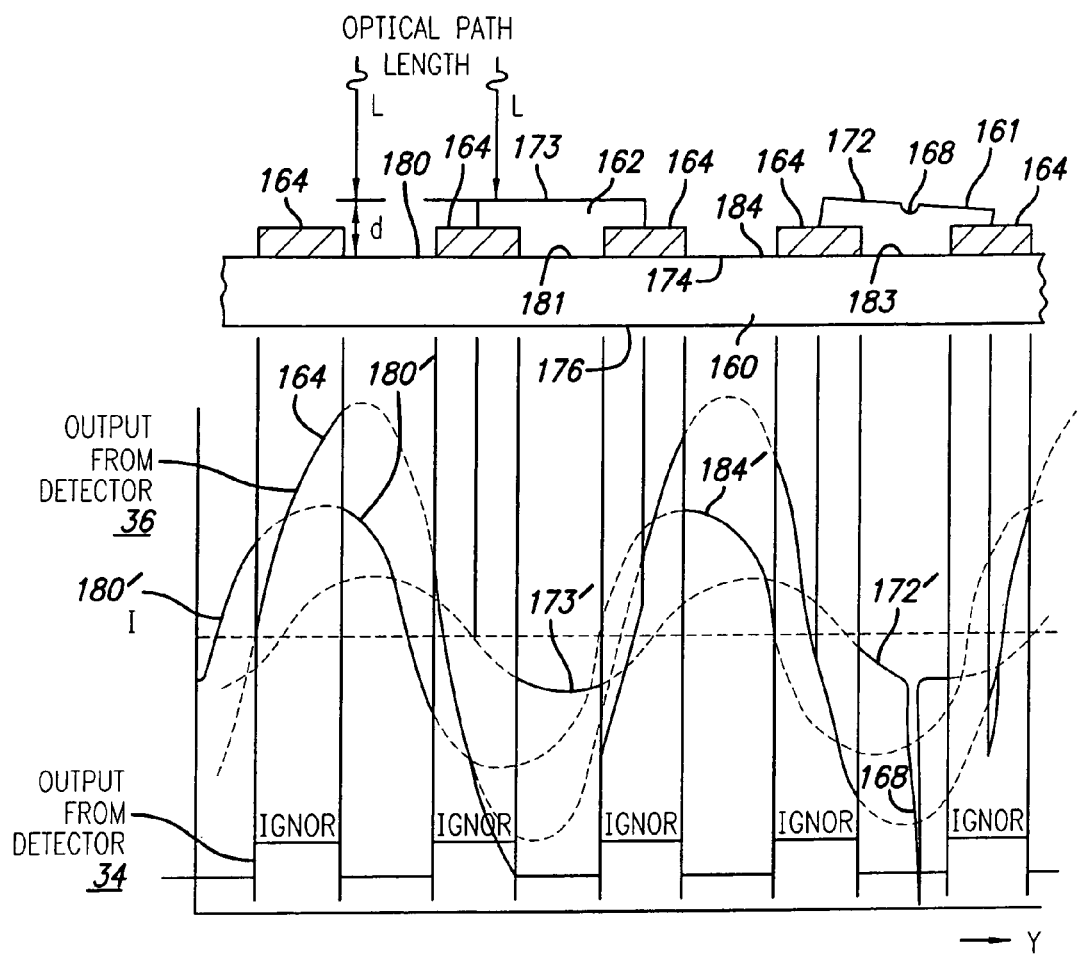
FIG. 10 is an illustration of a cross-section of a typical phase-shift mask showing in exaggerated scale an illustration of the phase-shifted output of the reflected beam detector.

FIG. 10 is an illustration of the cross section of one type of a phase shift mask. While the present example relates to a particular type of mask, on all types of masks, control of the thickness of phase shift material is a requirement and hence the technique described here is applicable to all types of phase shift masks.

The substrate 160 is typically of quartz on which opaque features 164 are deposited. These are typically thin layers of chrome. Phase shift features 161 and 162 made of transparent material will typically partially overlay part of the chrome 164 and some of the clear areas 181 and 183 between the features 164. Phase shift material filled transparent areas 181, 183 and clear areas 180, 184 typically alternate. The height of the upper surface 173 of the phase shift feature 162 above the level of the front, or upper, surface 174 of the quartz substrate is typically such that it produces a phase shift of 180 degrees with respect to a point 180 in the same plane but not covered by phase shift material.

Defects in phase shift masks may occur in several ways. There can be defects in the transparent areas, such as either excess chrome or dirt, or there can be missing chrome in a feature 164. Such defects are detected by the transmitted light detector 34 (FIG. 2) and are the subject of previously referenced publications. Defects may also be detected in the phase shift layer 161 or 162. There are two types of defects: those where there is a sudden variation of thickness of the phase shift layer, and those in which there is a deviation from the desired thickness which is either constant, or varies slowly over the phase shift layer. This occurs as the divot 168 in layer 161 is detected by the transmitted light detector 34 because it scatters the light and hence does not allow the light to pass through the phase shift material. The defect therefore appears as a dark spot in transmission. Slowly varying surfaces 172 or incorrect thickness of the phase shift layer, such as depicted in feature 161, are detected by interferometric methods, as explained below.

A perfectly flat surface, such as 173 at the top of 162, parallel to the plane of the mask and with an optical path length L will produce fringes as the mask is scanned because, due to the tilted mirror 118, the wavefront of the reference beam is not parallel to the plane of the substrate. (In order to avoid any ambiguity in the direction of the change of the phase, the tilt of mirror 118 should be greater than the maximum expected slope of any surface such as 161.) The detector output in such a case is a sine wave, such as that shown in FIG. 11. A similar flat surface located at a path length L+d (see FIG. 10) will produce a sine wave of the same frequency but with a phase shift D with respect to curve 200. This second sine wave is shown as wave form 202.

As the mask is scanned in the Y-direction, the transmitted light detector 34 detects whether a particular pixel is fully transparent. Only at such fully transparent pixels are reflected light intensity measurements taken and digitized. At such pixels, the reflected light intensity is determined and digitized. This is suggested by the depiction at the bottom of FIG. 10, where during the time that the scan is passing across the non-transparent feature 164, as determined by the output of detector 34, the output of detector 36 is ignored. From the intensity value, and from the Y-coordinate of the pixel, together with the values of A, w and $I_o$ determined during the calibration, electronic subsystem 20 determines D in Equation 2 and the corresponding path length variation at the pixel, i.e., the height d of the feature surface above plane 174.

Due to the periodic nature of a sinewave, there is an ambiguity because path length variations corresponding to a phase shift of 360 degrees are indistinguishable. However, sudden variations resulting in a 360° phase shift can occur only when the phase shift material contains a ridge. Such a ridge produces diffraction which is then detected in the transmission mode. Hence, the ambiguity due to a 360° phase shift is resolvable and it is possible to continuously, at every pixel, track the thickness of the phase shift material.

In practice, the mask substrates are not likely to be perfectly parallel to the image plane, nor is the substrate likely to be perfectly flat. However, these variations are gradual, and on a 5× phase shift mask one need consider variations only within a radius of 4-5 microns. Specifically, only the relative phase shift between two adjacent features is important, such as the relative phase shift between locations 180, 162 and 184. These points are likely to be less than 4 microns apart.

To determine whether there is a phase error of sufficient magnitude to indicate a defect on the substrate, the path length is computed at each transparent pixel covered by phase shift material 162 (FIG. 10). This value is then compared with the average of the path lengths of two adjacent points where there is no phase shift material, such as points 180 and 184. If the difference in path length differs from an acceptable value by more than a predetermined threshold value at the print wave length, such as 10 degrees for example, the phase shift material thickness at the inspected point is marked as defective.

In addition to making path length comparisons between points on geometric features in the same vicinity, the system also checks for a missing or extra geometric feature, such as may occur in the pattern generation. In die-to-die mode, the path lengths of pixels at 173, 180 and 184 (FIG. 10) of the die 33 (FIG. 3) are compared with the path lengths at the corresponding pixels of die 35. This comparison will disclose any missing geometric features, unless both dice 33 and 35 have the same error. Similarly, in die-to-database mode a comparison can be made between the path lengths associated with the previously designated pixels and the description of these pixels in the CADs database.

Alternate Phase Shift Measurement Method

The above measurement technique uses a digital approach to determine the relative optical path length at grid points to determine the phase shift angle at every point. As explained below, one may also employ an analog method to find the phase shift angle.

Figure 12:
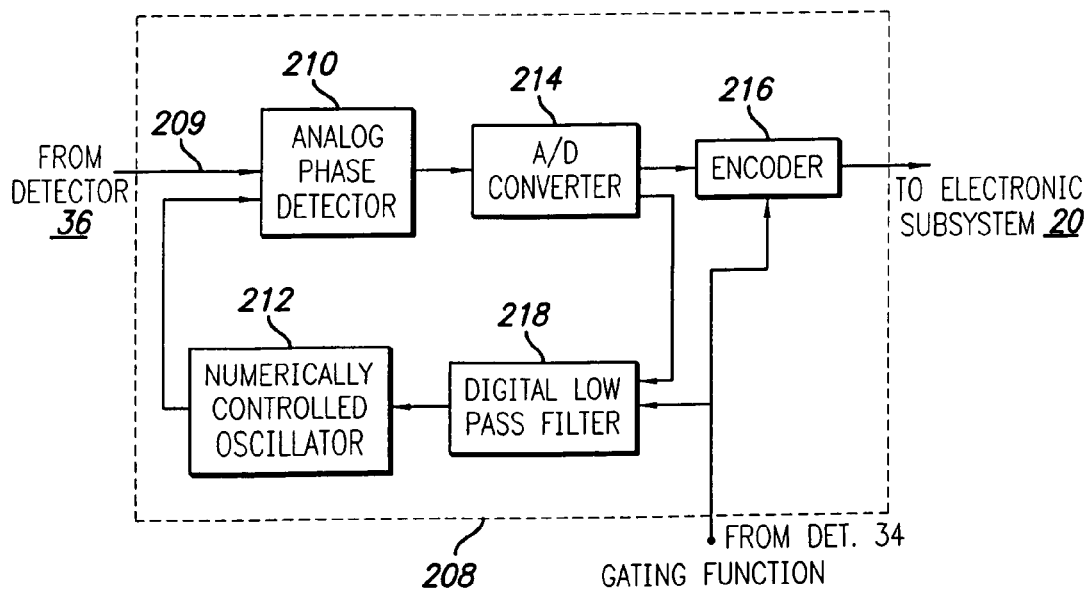
FIG. 12 is a block diagram depicting a phase-locked loop subsystem used to detect phase-shift material thickness.

FIG. 12 illustrates the additional circuitry required by this method for insertion into the apparatus of FIG. 1 at 208 to determine the phase shift angle. The analog signal derived from detector 36 is fed to one input 209 of an analog phase detector 210 which also obtains another signal at 211 from a numerically controlled oscillator 212. A signal proportional to the phase difference between these two signals is converted to a digital form by an eight bit A/D converter 214 and passed to an encoder 216 and also to a digital low pass filter 218. The digital filter 218 and the encoder 216 are gated by a gating signal derived from detector 34. The digital filter 218, which functions as an integrator, accepts an input only when detector 34 indicates that the mask is transparent at the inspected point. Encoder 216 accepts the 8-bit output signal of the A/D converter 214 and shifts it right one bit. If the pixel is transparent at that point, the encoder inserts a 0 into the most significant position of the digital signal and transmits the remaining signal to subsystem 20 as the phase signal. Should detector 34 indicate that the pixel is opaque, the digital signal will be encoded as all ones, 11111111. This signifies to the subsystem 20 that the phase signal is invalid and should be disregarded.

The previously explained circuitry is a phase-locked-loop that follows slow variations of the phase, as might be caused by slowly varying phenomena, such as imperfect flatness of the mask. The output of the encoder 216, when valid, indicates the path length variation in the local area.

Alternate Phase Shift Optical System Implementation

Figure 13A:
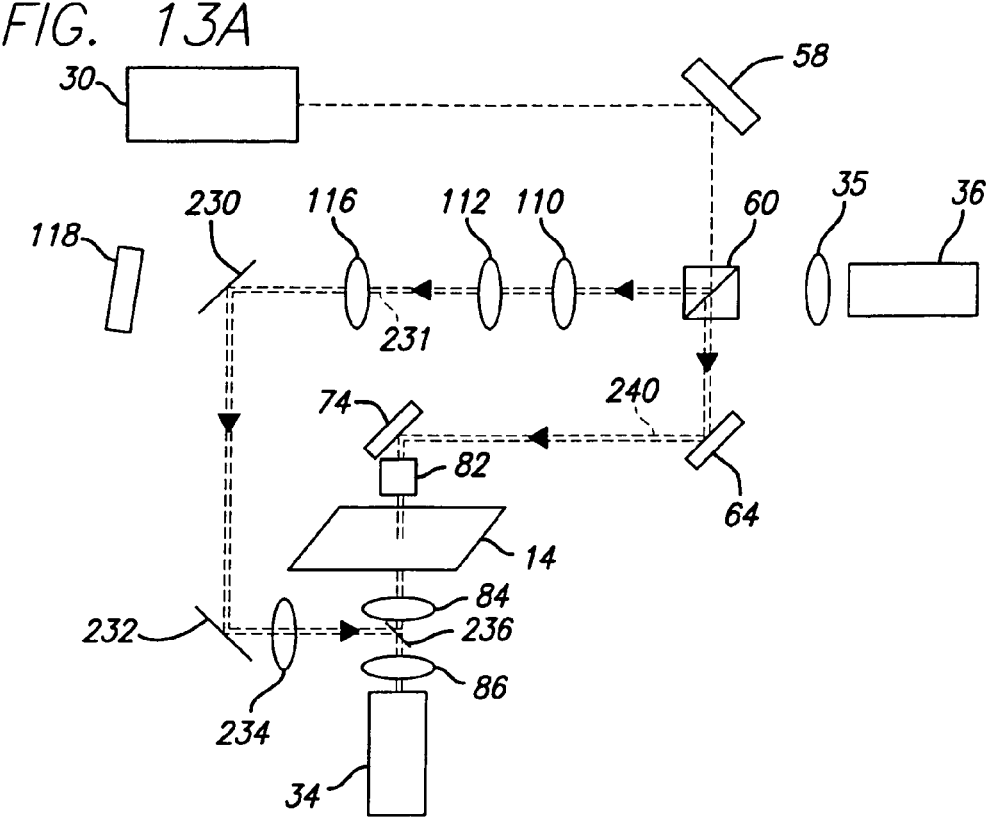
FIGS. 13a and 13b are simplified schematic diagrams respectively depicting operation of the optical subsystem used for measuring the phase-shift material thickness in the transmitted and reflected light modes.
Figure 13B:
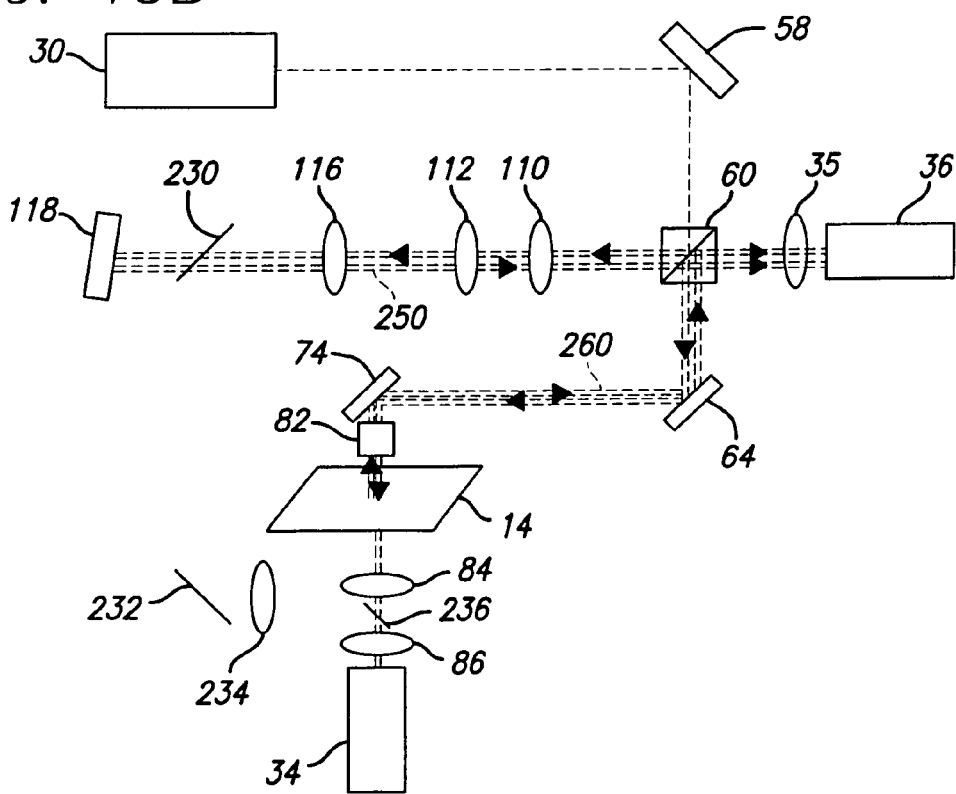

In some instances it is desirable to measure the actual phase shift, rather than infer the phase shift from the relative path length. This may be done by using transmitted interferometry. FIGS. 13a and 13b are simplified schematic diagrams, in which for simplicity many of the elements shown in FIG. 2 are omitted, but illustrate a variation of the preferred embodiment that permits measurement in either or both a transmit mode or a reflected mode using respectively transmitted light interferometry and simultaneous measurement of the reflected and transmitted interference pattern.

As depicted in FIG. 13a, to implement this alternative operating in the transmit mode, a pellicle beam splitter 230 is added which reflects light received from splitter 60 and produces a reference beam at detector 34 via the path 231 past tilted mirror 232, objective lens 234 and another beam splitter 236. The interference of the reference beam and the imaging beam passing along path 240 and through substrate 14 is detected at detector 34.

In the reflected light mode, reference light split by splitter 60 is directed along the path 250 to tilted mirror 118 and returned to detector 36 where it interferes with imaging light passing through splitter 60 and along the path 260 to substrate 20 where it is reflected back along path 260 and reflected by splitter 60 into detector 36.

This alternative also permits the simultaneous measurement of the phase in both the reflected and transmitted modes.

Because lasers have a limited coherence length in both the reflected and transmitted interference modes, the path length should be approximately the same for the imaging beam path and the reference beam path.

Line Width Measurement

Figure 14:
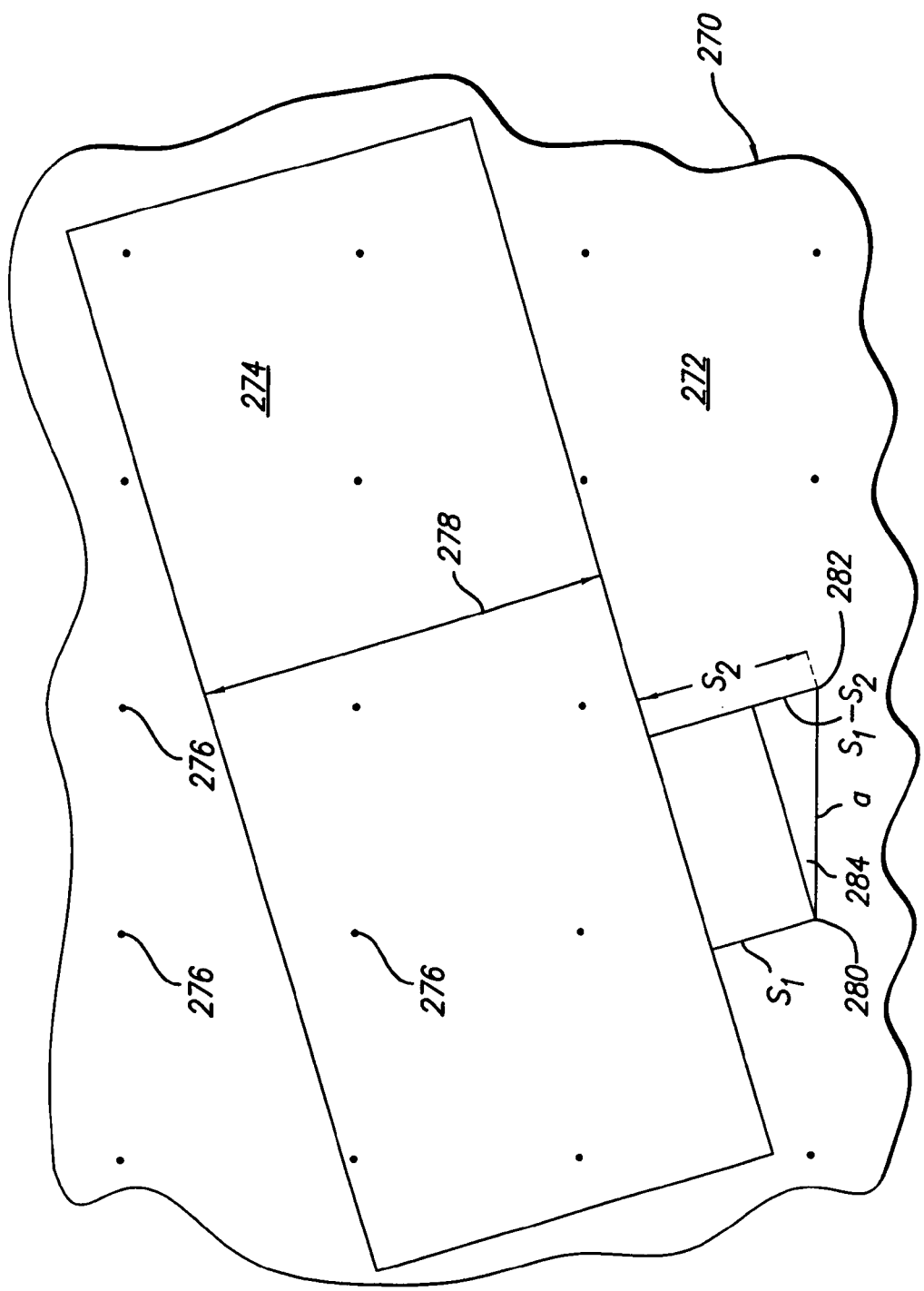
FIG. 14 is an illustration used to describe the method of line width measurement.

FIG. 14 shows a plan view of a small portion 270 of a mask. Area 272 is transparent and is crossed by a feature 274 that may either be opaque (chrome or other material) or transparent if the quartz substrate of the mask is covered by phase shift material. The system measures the intensity at equidistant grid points, depicted at 276. As explained more fully below, these intensity measurements are then used to determine the line width, i.e., the distance 278 across feature 274.

Each of the grid points 276 the intensity is the convolution of the point spread function of the optical system with the transmissivity profile of the feature. Typically, the transmissivity profile is a step function. Therefore, for a straight feature, as is shown in FIG. 14, the intensity measured at a particular grid point is a function of the perpendicular distance from the grid point to the edge of the feature (line 274). The intensity at a particular point in the vicinity of a feature can thus be interpreted as the perpendicular distance from the point to the line. This interpretation is done in a simple table look-up operation in the computer 24 (FIG. 1). On the basis of the intensities at grid points 280 and 282, distances $S_1$ and $S_2$ are known and the slope of the edge relative to a feature is:

$$\tan G = \frac{S_2 - S_1}{(a^2 - (S_2 - S_1)^2)^{1/2}}$$

where a is the distance between the grid points 280 and 282 and G is angle 284.

Once the slope of the edge of a feature (line) has been determined, the opposite edge of the line can be similarly located, and a verification can be made that it is parallel to the previously calculated line edge. On the basis of the intensities along the two edges of the line, the linewidth is calculated in control computer 24.

The previously described method of line measurement is, strictly speaking, normally applicable only to conventional masks which have no surface areas covered by phase shift material. However, the technique described above may also be used for the measurement of phase shift features because, at the boundary between a clear area and an area covered by phase shift material, diffraction of the incident light beam will occur and along this narrow boundary no light will be transmitted. The line width is the distance between the center of one boundary and the center of the opposite boundary.

It is anticipated that various alterations and modifications thereof will be apparent to those skilled in the art. For example, to avoid the need to sweep the laser beam during the scanning operation, instead of using the linear detector 34 in the preferred embodiment, one could use a time delay integrating sensor of the type described in the above-referenced Levy U.S. Pat. No. 4,579,455. With such modification, if a laser is used as the light source, coherence in the Y-direction would have to be destroyed by using a rotating ground glass. The coherence in the X-direction is destroyed by the time delay integrating sensor.

The system further includes an inspection system and method that represents a major departure from the traditional die-to-die comparison method of substrate inspection. With the well known and widely used die-to-die (or die-to-data base) comparison technique, the characteristics of the substrate under inspection are compared to another like substrate or a data base that is known to be correct. That requires the simultaneous processing of the same information with two optical columns for the die-to-die for both the die under inspection and the sample to which it is being compared which is both hardware and computer processing intensive.

As will be seen in the discussion that follows, the second aspect of the system performs all of the inspection tasks using only a single optical column and only the substrate to be inspected. This is accomplished by analyzing the relationship between two or more of the transmitted and reflected light signals from that substrate and derived functions of those signals, the relationship between those light signals, and the relationship between each of the transmitted and reflected light signals and the second derivatives of those light signals.

APSM/EPSM System Overview

Figure 15:
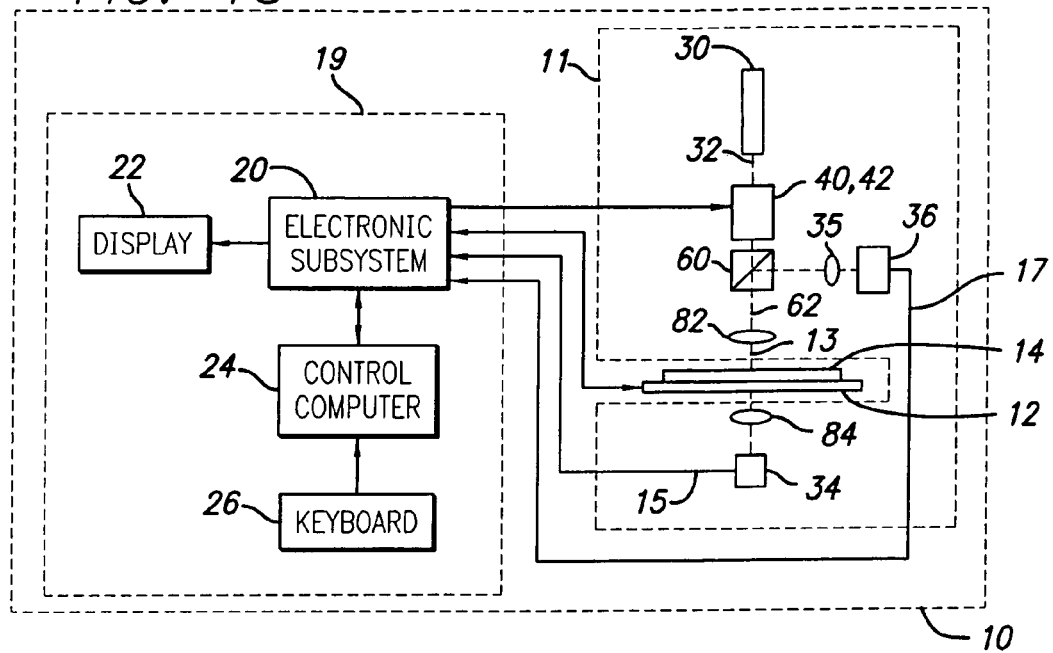
FIG. 15 is a simplified functional block diagram of the laser mask inspection system of the second aspect of the present invention and a modification of FIG. 1.
Figure 16:
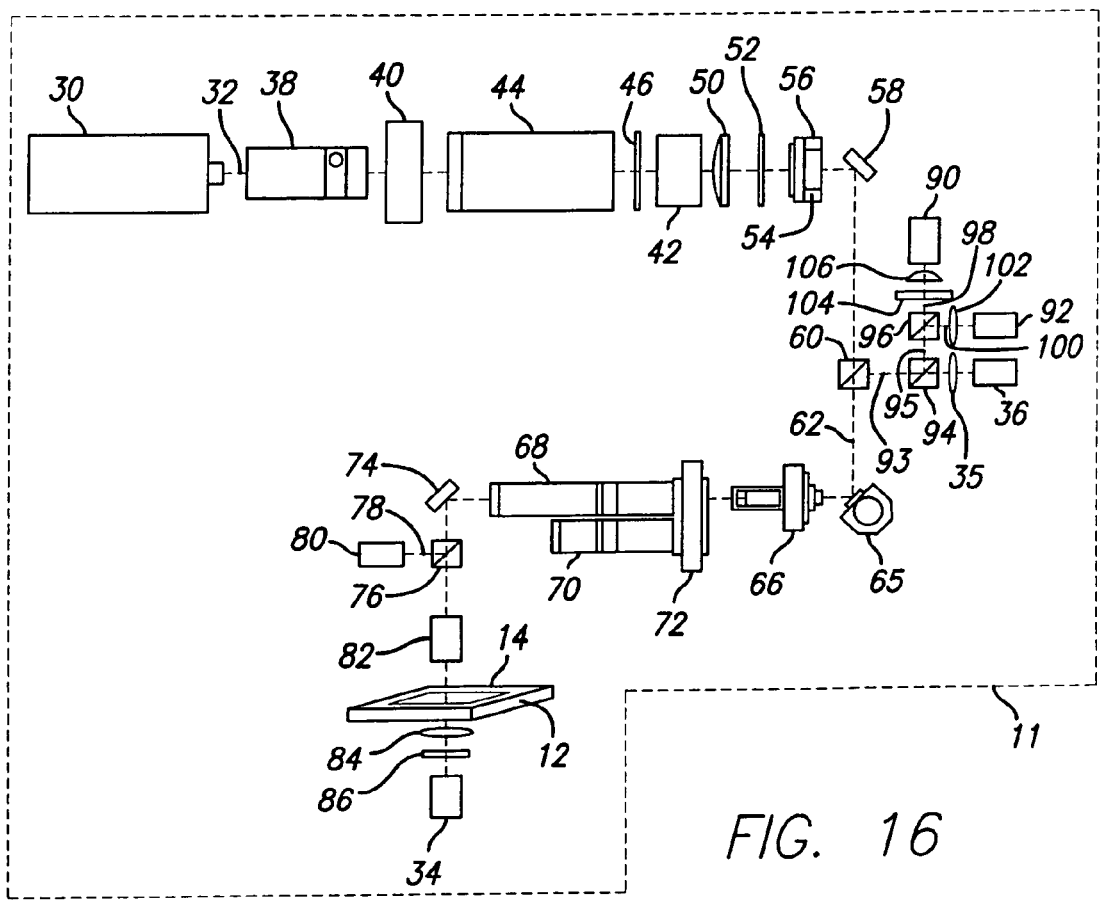
FIG. 16 is a more detailed schematic representation of the optical subsystem depicted in FIG. 15 and a modification of FIG. 2.

The basic structure of the APSM/EPSM system is shown in the simplified view of FIG. 15 and the more complete view of FIG. 16. This system is very similar to the simplified and detailed FIGS. 1 and 2. The difference between FIG. 1 and FIG. 15 is that data base adaptor 18 is not required needed for the current aspect of the system. Similarly, the difference between FIGS. 2 and 16 is that the phase shift/line width measuring components that extend to the left from beamsplitter 60 are not necessary to perform the function of the current aspect of the system. The phase shift/line width measurements could be performed using the same transmission data as that used for inspection by the technique of the current aspect of the system. From FIGS. 15 and 16 it can be seen that the automatic optical inspection system 10 includes three specialized subsystems: a laser/optical subsystem 11; an x-y stage and servo drives 12 subsystem; and an electronics control and display subsystem 19. FIG. 15 also shows a substrate 14 on X-Y stage 12 that is to be inspected for defects.

Transmitted and reflected light inspections can be performed either simultaneously or mutually exclusively in time with the requirements for the illumination light beam on, and the position of, substrate 14 being as discussed above.

Briefly, the underlying theory of operation, which is discussed more completely below, is the ability to compare signals corresponding to at least two of the detected transmitted and reflected light beams and functions of each of them being able to disclose the existence of a defect. The two measured values of the system are the intensity of the light beam transmitted through the substrate as sensed by transmission detector 34, and the intensity of the reflected light beam as detected by reflected light detector 36. Those two measured values can then be processed to disclose the type of defect, if any, at a corresponding point on the substrate. As an example, either a chrome dot or a particle on a substrate is opaque and hence will result in a "dark output" (low signal output) from transmission detector 34, with the reflective chrome dot defect on the substrate producing a high reflected light indication while the particle will typically reflect less. Thus, the use of both reflective and transmissive detection, for example, one may locate a particle on top of chrome geometry which could not be located if only the reflective or transmissive characteristic of the defect was examined. In general, one may determine signatures for certain types of defects, such as the ratio of their reflected and transmitted light intensities. This information can then be used to automatically classify defects.

X-Y Stage and Servo Drives 12

X-Y stage 12 is a precision substrate driver under control of electronic subsystem 20 and capable of moving substrate 14 under test in a serpentine fashion, within a single plane, relative to the optical axes of optical subsystem 11 so that all, or any selected part of, the substrate surface may be illuminated and therefore inspected.

In a typical inspection system of the second aspect of the present invention, stage 12 is an air-bearing X-Y stage that is driven by a linear motor, or servo, on each axis with the position of stage 12 along each axis monitored by interferometers (not shown), such as a model TIPS V, made by Telectrac Corporation.

Electronics and Control Subsystem 19

The electronics and control subsystem 19 includes several elements shown in FIG. 1. Included are electronic subsystem 20, control computer 24, keyboard 26 and display 22. Keyboard 26, in communication with control computer 24, and display 22, in communication with electronic subsystem 20, provide the user interface to the inspection system of the second aspect of the present invention. Additionally, electronic subsystem 20 is in communication with x-y stage 12, transmission and reflected light detectors 34 and 36, and control computer 24.

Control computer 24 acts as the operator console and master controller of the system and is a device such as a SPARC computer made by Sun Microsystems of Mountain View, Calif. with all system interfaces with the operator and the user's facilities made through control computer 24.

Commands are issued to and status is monitored from all other subsystems and components so as to facilitate completion of the operator assigned tasks.

The function of electronics subsystem 20 is to interpret and execute the commands issued by control computer 24. These functions are: digitize the input from transmission and reflected light detectors 34 and 36; compensate these readings for variations in the incident light intensity; accumulate the output of the interferometers used to track the stage 12; provide the drive for the servos of stage 12; and monitor sensors which indicate status.

Operational Theory

Transmission detector 34, instantaneously and continuously, generates a transmitted light signal 15 in proportion to the light transmitted through substrate 14 and received by transmission detector 34. Transmitted light signal 15 is then amplified and offset in electronic subsystem 20 to normalize the peak-to-peak signal amplitude to values of 0 to 1. Similarly reflected light detector 36, instantaneously and continuously, generates a reflected light signal 17 in proportion to the light reflected from substrate 14 and received by reflected light detector 36. Reflected light signal 17 is similarly normalized in electronic subsystem 20.

For purposes of discussion, substrate 14 is assumed to have an opaque layer that covers a portion of the underlying material of substrate 14. That opaque layer will reflect a greater portion of incident laser light 13 than is similarly reflected from the surface of the bare underlying material of the substrate. For example, it is known in the art that at a wavelength of 488 nm, anti-reflective chrome (opaque layer) has a reflectance of 11% and quartz underlying material of a substrate has a reflectance of 4.5%.

Figure 17:
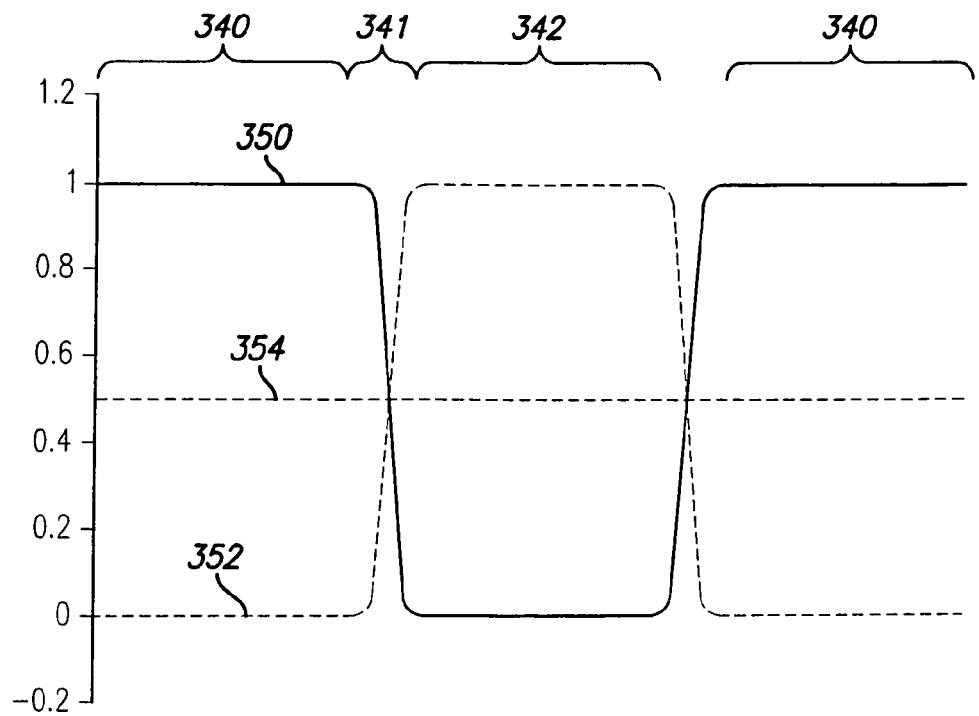
FIG. 17 is a normalized plot of the transmitted light and reflected light signals detected by sensors of the second aspect of the present invention for one scan of the laser scanner.

FIG. 17 illustrates a hypothetical model for the normalized transmitted and reflected light signals 350 and 352, respectively, for a scan across a substrate with the abscissa of FIG. 17 being time, or distance across substrate 14, as light beam 13 is advanced relative to the surface of substrate 14. When light beam 13 scans a bare section of substrate 14 having a quartz underlying material, the normalized transmitted light signal 350 is at level 1 and the normalized reflected light signal 352 is at level 0, as shown in region 340 of FIG. 17. The ordinate associated with FIG. 17 therefore represents the grey scale of the transmission or reflection. When light beam 13 scans a region of substrate 14 having an opaque layer, the normalized transmitted light signal 350 is at level 0 and the reflected light signal 352 is at level 1 as shown in region 342 in FIG. 17. In the case where light beam 13 is at an edge of an opaque layer, or feature, on substrate 14, the normalized transmitted light signal 350 transitions from level 1 to level 0 while the normalized reflected light signal transitions from level 0 to level 1 as illustrated in region 341 of FIG. 17.

This hypothetical model assumes that the transmitted and reflected signals at the same point on substrate 14 are always complementary to each other in the absence of defects, so that their sum 354 is also invariant in the absence of defects. This behavior is represented in FIG. 17 by summation signal 354, which is offset by 0.5 from each of signals 350 and 352. Thus, such behavior would allow any observed deviation in the summation signal to be interpreted as a defect detection.

Figure 18:
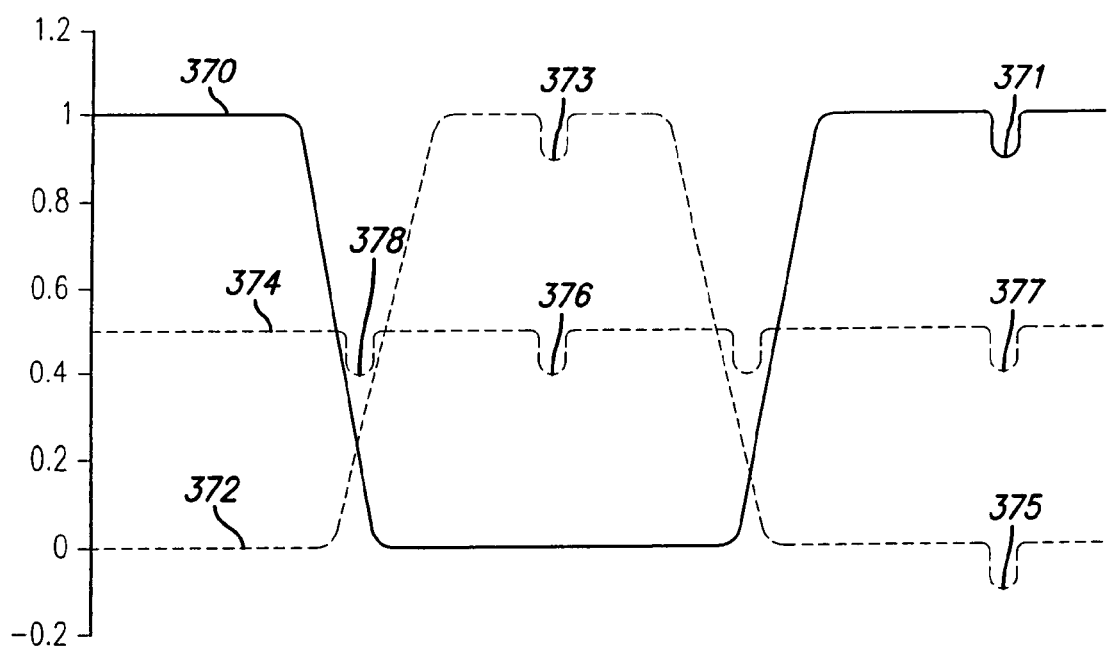
FIG. 18 is a normalized plot of the transmitted, reflected, and summation signals for a optical subsystem of the second aspect of the present invention showing the effect of particulate contamination on those signals.

Referring now to FIG. 18 the typical signals observed for a realizable optical subsystem are illustrated in a manner similar to that of FIG. 17.

Included are transmitted light signal 370, reflected light signal the left most region that corresponds to region 340 of FIG. 17. In that region of FIG. 18 the signal values are typical for inspection over the clear substrate with no opaque overlayer or defects present. In the center region of FIG. 18, a blip 373 in the normalized reflected light signal 372 and a resultant blip 376 in the summation signal 374 both result from a particulate contamination on top of an opaque layer on substrate 14. In the right most region of FIG. 18, blip 371 in the normalized transmitted light signal 370, the corresponding blip 375 in the normalized reflected light signal 372, and resultant blip 377 in the summation signal 374 all are caused by a particulate contamination on a transparent substrate 14.

In such a situation as shown in FIG. 17, summation signal 374 also deviates from the constant 0.5 level in the transition regions (similar to regions 341 in FIG. 17) of the plot. These transition regions correspond to those portions of substrate 14 that are near the edges of features thereon (e.g. boundaries between opaque layers on the substrate and bare underlying substrate regions). Such a deviation appears in FIG. 18 as blip 378. Deviations such as blip 378 are due to variations in the light scattering behavior at edges of features on substrate 14, and mismatches between the partial coherence parameters of the transmitted and reflected optical paths (see FIGS. 15 and 16). Typically these deviations in the summation signal at feature edges can be of roughly the same size as a blip 377 caused by submicron contamination on substrate 14. Therefore, detection of defects by the summation of the reflected and transmitted light signals 17 and 15, respectively, does not provide an adequate method for distinguishing submicron particulate contamination from feature edges on substrate 14.

One extension of the method to enable a realizable optical subsystem to automatically distinguish between surface features and defects of a substrate 14 is discussed below in relation to FIGS. 19-22.

Figure 19:
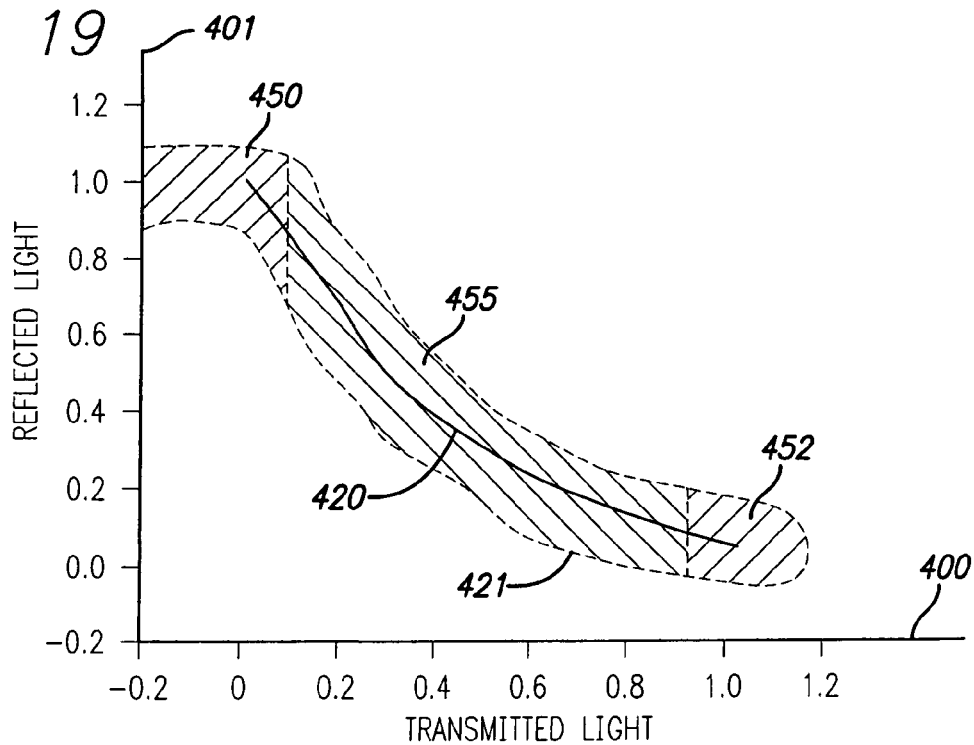
FIG. 19 is a graph of the relationship between transmitted and reflected light signal pairs in the absence of defects as per the second aspect of the present invention.

FIG. 19 illustrates the relationship between a family of pairs of normalized transmitted and reflected signal values with each pair of values occurring at a particular point on the surface of substrate 14 as light beam 13 is deflected over substrate 14, showing the correlation between each of the two signal pairs with no defects present at any point on substrate 14. In FIG. 19 the normalized transmitted light signal is plotted on abscissa 400 and the normalized reflected light signal from the same point on substrate 14, is plotted on ordinate 401 for each pair of signals from each inspected point on substrate 14.

As discussed above in relation to FIG. 15, electronic subsystem 20 normalizes and offsets the transmission and reflected signals 15 and 17 to range between 0 and 1. Thus, for example, region 450 of FIG. 19 represents signal pairs from a substrate region where there is a much greater reflected signal than transmitted signal which could represent an opaque layer on the substrate at that point. This results since an opaque layer attenuates the light beam resulting in a small light transmission value, and at the same time, that opaque layer reflects approximately 11% of the incident laser beam to reflected light sensor 36. Similarly, region 452 of FIG. 19 can be seen to represent the condition where laser beam 13 scans a bare region of a quartz substrate. Values in region 452 result from a point on substrate 14 that transmits a large portion of light beam 13 resulting in a high detected transmitted light value, while at the same point on the substrate only about 4.5% of the incident laser beam 13 is reflected resulting in a small detected reflectance value. Thus, the intermediate region 455 in FIG. 19 represents points on the surface of substrate 14 where light beam 13 is scanning the edges of features.

A typical transmission-reflection relationship in T-R space (the coordinate plane defined by T and R orthogonal axes) for a realizable optical system is shown by curve 420 enclosed within a uniform tolerance area defined by envelope 421. (Note that the shape of curve 420 will vary depending on several factors: the operational characteristics of optical subsystem 11; as well as the materials of the underlying layer and surface layers of the features of substrate 14. Each combination of optical subsystem and substrate design therefore will have its own characteristic curve 420 in the T-R space.)

Thus, each inspectable point, or pixel, on substrate 14 can be represented in the T-R space by a point with coordinates corresponding to the transmitted and reflected signal values produced at that pixel. Those pixels with transmitted and reflected signal values which fall within tolerance envelope 421 are considered to be defect free while all others represent either defects or system noise. The tolerance to which the inspection is to be performed, and hence which transmitted and reflected pixel pairs will be considered defective, is determined by the width of envelope 421 and the distance of its boundary from curve 420. The width of envelope 421, and hence the inspection tolerance, can be varied parametrically by position along curve 420 so that a user may establish a tighter tolerance against more harmful types of defects and a more relaxed tolerance against other types of defects. For example, the defect identification sensitivity over bare areas of the substrate can be independent from the identification sensitivity of defects over the opaque areas of the substrate. One could even have a complex set of tolerances that span the entire T-R space (i.e. the width of envelope 421 does not have to be uniform along T-R curve 420).

Thus, one feature of the second aspect of the present invention is a T-R space coordinate plane as in FIG. 19. Thus, if the T-R point for any point from substrate 14 falls outside the selected tolerance envelope defined by boundary 421, a defect is identified whether or not the actual coordinates of the point of the defect are known. Keep in mind that there has as yet been no discussion in this section of the specification of the alignment of the substrate and the maintenance of any coordinates of defects in memory. Since the present inspection system is not a comparison system, as in the prior art, it is not necessary to know the physical location of a defect on the substrate to determine that there is a defect. All one needs to do is to select the tolerance that is acceptable for each type of surface characteristic and if a T-R measurement falls outside of envelope 421 the substrate is defective. It is also not important to the method of the current aspect of the system that the points in the T-R space be contiguous for the method to find defects. For example, the first point may fall in region 450, the next 55 points within region 425, then 6 points in region 450 again, one point in region 455 and then 2 points in region 452, etc. The sequence is unimportant to the ability of the second aspect of the present invention to identify the presence of a defect.

Also, as discovered during the development of the second aspect of the present invention, the location of the T-R point in the T-R plane also conveys information about the physical properties of the pixel element on the surface of the substrate and, in the case of a defect, the type of defect found. Thus another feature of the second aspect of the present invention is the use of the T-R detection space for automatic defect classification.

Given that discovery, the defect detection process of the second aspect of the present invention includes at least the ability to identify defect types using T-R space. To do so, the non-defective region in T-R space defined by boundary 421 must be determined so that any T-R pair for an inspected pixel on substrate 14 can be instantly determined as a defect or a non-defect point by whether it falls inside or outside the non-defective region within boundary 421. Furthermore, the location of the T-R point could, if desired, be analyzed to identify the type of defect that was detected.

Methods for bounding the non-defective region and the various defect classification zones, collectively referred to as the T-R reference map, are discussed further below. Additionally, since the defect detection process depends only on the two measured signals T and R at a single point of the substrate, and does not depend upon the comparison of test and reference images (die-to-die or die-to-data base) as taught in U.S. Pat. No. 4,926,489, no alignment of the substrate with the defect determination system of the second aspect of the present invention is required.

It has been observed that the use of a global alignment step of the substrate to a reference grid would further enable the system to determine the location of the defect on substrate 14 as well, if the user should so desire. However, as stated above, for a pass/fail defect determination test the physical location on the substrate of the defect is unnecessary.

Figure 20:
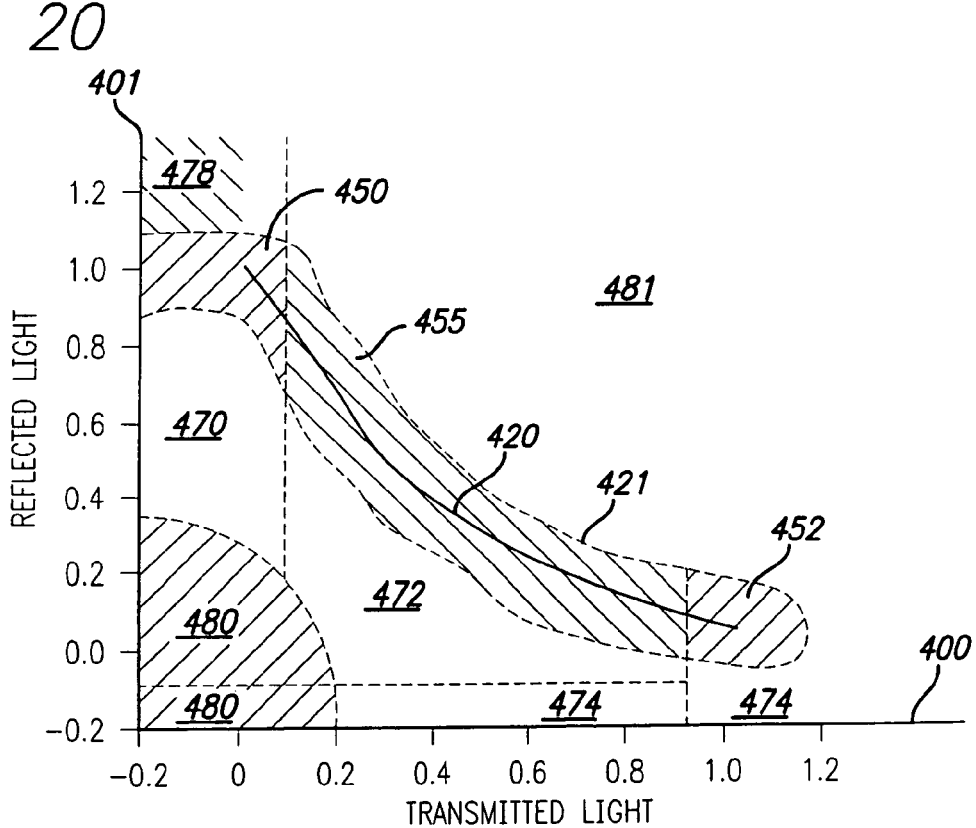
FIG. 20 is a graph as in FIG. 19 which shows the additional loci of points resulting from particulate contamination on the opaque layer, at the edge of a feature, and on the photomask substrate as per the second aspect of the present invention.

FIG. 20 is a plot of a typical T-R reference map that illustrates various defect regions which one might encounter with the type of substrates currently of interest. For example: particulate contamination on anti-reflective chrome would have low T values and intermediate R values as represented by region 470; particulate contamination on an otherwise bare quartz region would have low R values and intermediate to high T values as represented by region 474; particulate contamination on the edge of a feature could have a broad range of T and R values from both being low to one being high while the other remains low as represented by region 472; a missing anti-reflective chromium layer would have a high R value and a low T value as represented by region 478; very large defects would have very low values of T and R as represented by region 480; and the presence of thin residual chrome transmission defects would have T and R values that are to the right and above characteristic curve 420 as represented by region 481.

For some types of defects, analysis of the T-R point may not be a sensitive enough indication of the presence of a defect (i.e. the variation of either the T or R value may not be sufficiently indicative of a problem given the corresponding other value for a particular pixel on substrate 14). An example of this type of defect is an inclusion in a quartz substrate, wholly contained below the surface of a mask. In that type of defect the change of the transmission value, T, occurs with little or no corresponding change in the reflectance value, R. As can be seen from FIG. 20, nominal reference curve 420 has a small slope for large T values. Therefore a change in the transmission value alone in this region may not result in a T-R point outside envelope 421 and hence will be difficult to detect, or go undetected, in T-R space alone.

Figure 21:
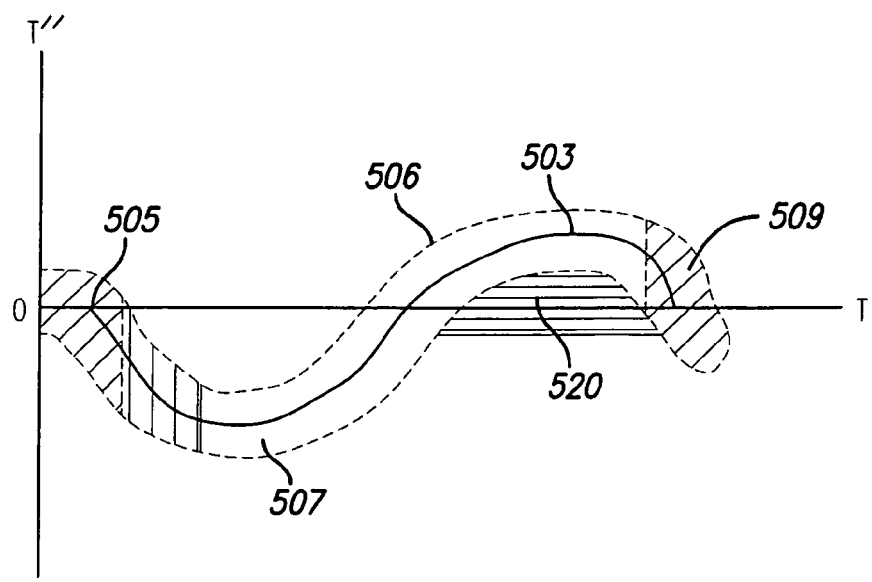
FIG. 21 is a graph of transmitted light values versus the second derivative transmitted light values as per the second aspect of the present invention.

However, if the second derivative of the normalized transmission value, T", which identifies the presence of edges in the image, is plotted against the normalized transmission signal, T, as in FIG. 21, those types of defects can be identified. The nominal behavior for pixels from defect-free points on the substrate correspond to the curve 503, enclosed by tolerance envelope 506 as shown in FIG. 21. The coordinate plane such as in FIG. 21 is referred to as the T-T" detection space, and is another feature of the second aspect of the present invention.

As with T-R space, T-T" reference map is derived by identification of the defect-free region, here within envelope 506, and other specific regions of interest in T-T" space. In this case, a change in transmission, resulting in a T-T" point within locus 520, outside the non-defective region in envelope 506, tentatively indicates a transmissivity defect, although such a point could occur when the pixel is located near the edge of a feature and not be a defect at all. Thus, T-T" space alone could not be relied on to make the necessary distinction in such a situation.

Figure 22:
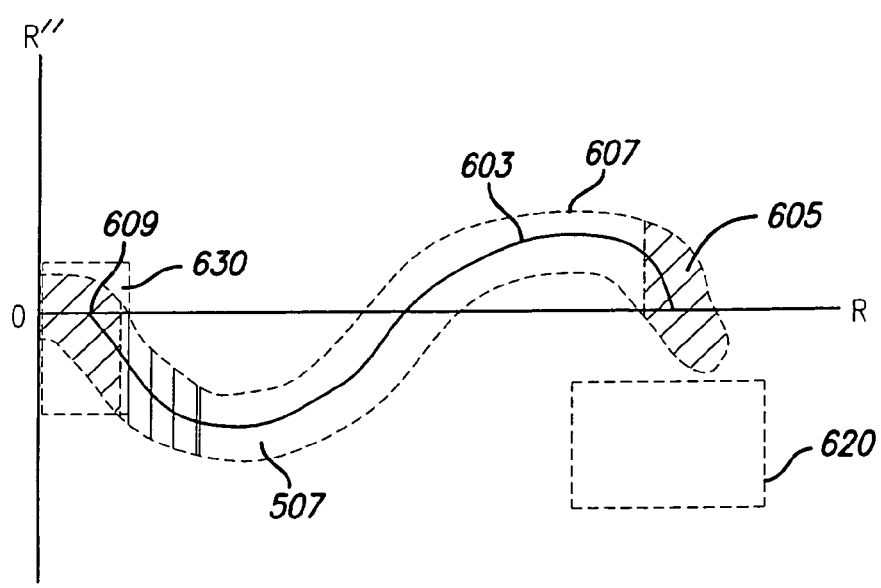
FIG. 22 is a graph of reflected light values versus the second derivative reflected light values as per the second aspect of the present invention.
Figure 24A:
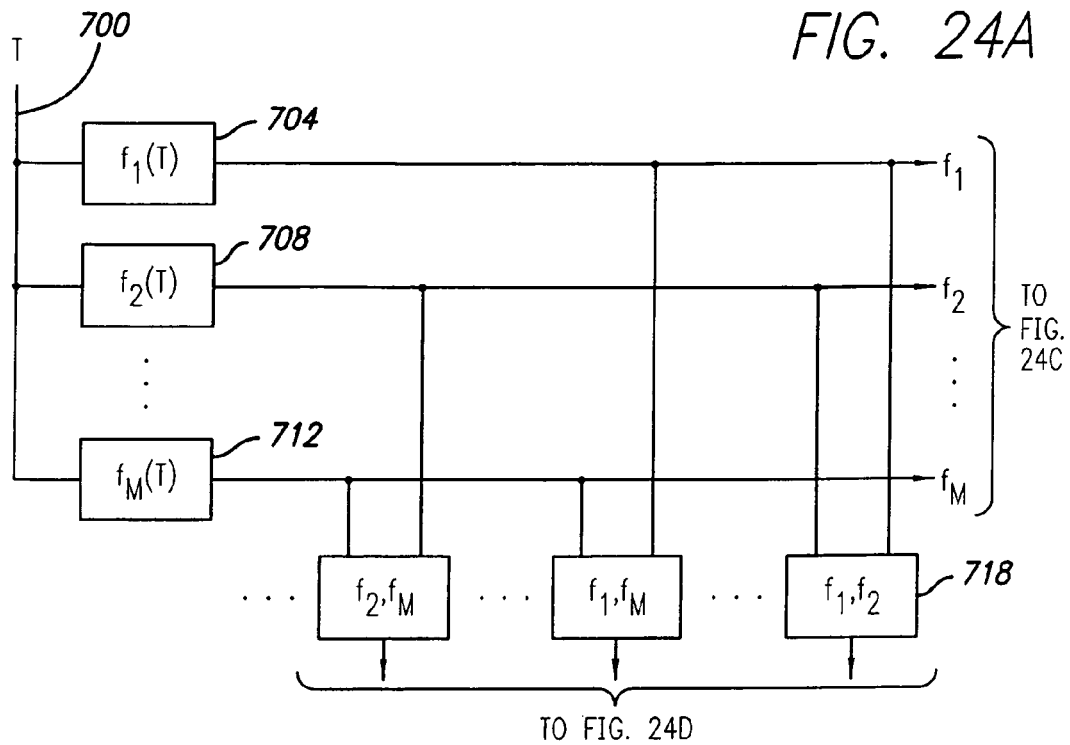
FIG. 24 is a block diagram shown in three tiers with the transmission and reflection observed pixel maps as input signals which are operated on by a selected number of different filters, the filter output signals being combined pair-wise in the second layer, and the third layer providing a merge function to identify all of the defects detected from each of the pair-wise signal combinations of the second layer.
Figure 24B:
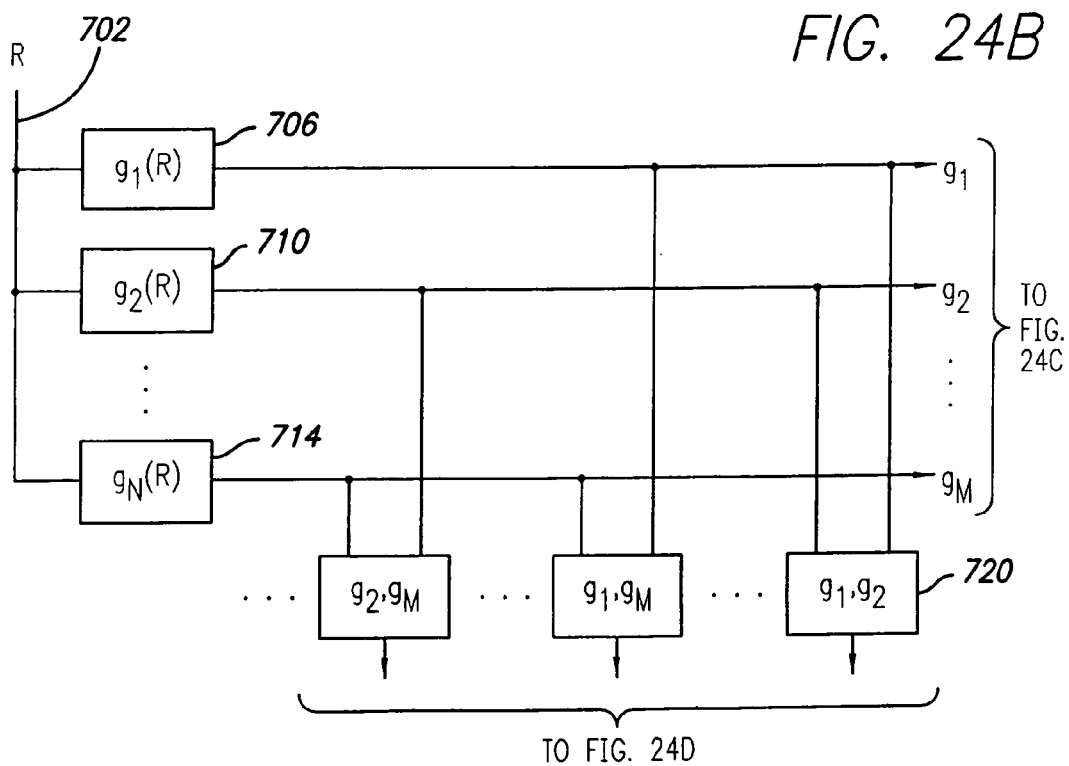
Figure 24C:
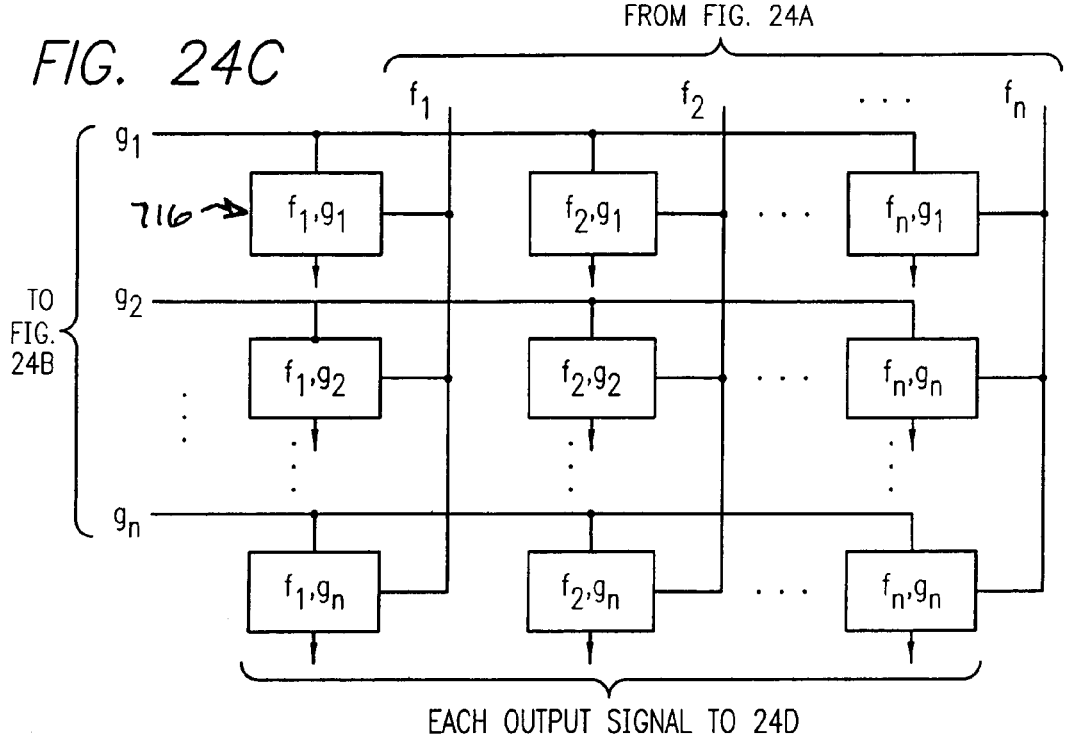
Figure 24D:
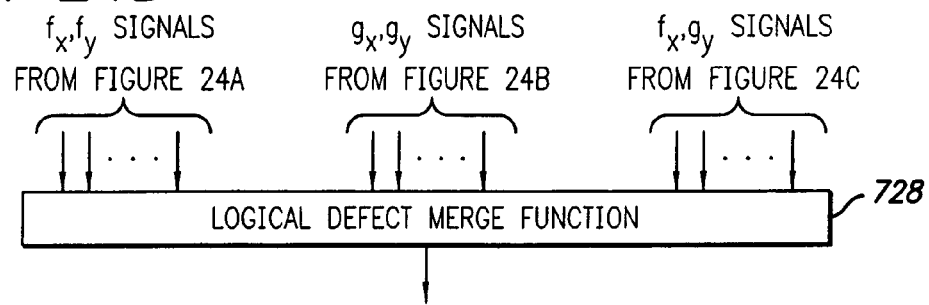

During the development of the system, it was also discovered that it may be useful to examine the reflected signal, R, plotted against the second derivative of the reflected signal, R". FIG. 22 similarly illustrates the R-R" space which is also a feature of the second aspect of the present invention. Curve 603 represents the nominal relationship between R and R", and region 607 represents the region of tolerance for non-defective pixels with the R-R" detection space also divided into distinct regions of interest. One of those regions of interest includes the tentative defect-free region within curve 607, to form an R-R" reference map. Other regions of interest include locus 605 with the points therein potentially resulting from the laser scanning an opaque layer where the R value is high, the T value low, and the value of R" is also low. Another region of interest is within locus 609 where points therein tentatively result when the laser scanning beam illuminates a point on a bare substrate. The third region of interest is the locus of points 630 which is typical of an illuminated pixel that is not positioned on the edge of a feature when there is a corresponding reading of that pixel in region 520 of the T-T" space (FIG. 21). With both of those conditions being met, the pixel of interest corresponds to a transmissivity defect on the sample. Finally, where there is a residue on an opaque layer, associated pixels in R-R" space will be in region 620, with the corresponding values of R and R" signifying the presence of a reflectivity defect.

Thus, to positively identify and classify as many defects of substrate materials at a point on a substrate, it is necessary to determine which defect regions are occupied by the coordinates of the point in each of the T-R, T-T", and R-R" spaces. With that information, electronic subsystem 20 can reduce coordinate information into region information and generate an independent defect region report for each space with a code to indicate the region (e.g. 452, 455, 470, 472, 474, 478, 480, 481, 505, 507, 509, 520, 605, 607, 620, 630, etc.) occupied by the coordinate in that space. Further, with such a region report available from each detection space, electronic subsystem 20 can then logically merge the region reports from each of the detection spaces to synthesize a final defect report that comprehensively encodes the results collected for that point on the substrate and reports whether a defect was indicated by those results. That final defect report would thus indicate a pixel type code and a binary defect indicator value that indicates whether or not a defect is present. With this information at hand, the system can also be programmed to produce other types of reports, including one that totals the number of points having each type of defect over the entire substrate.

Many defect types can be found simply by the occurrence of a defect indication falling within the coordinates of a defect detection region in only one of the two function spaces (i.e. T-R, T-T" or R-R" space). However, as explained above, for example, certain transmissivity defects can only be detected by an occurrence of a defect indication in both the T-T" space in region 520 (FIG. 21) that corresponds to a defect indication in R-R" space in region 630 (FIG. 22). In those instances, a final transmissivity defect report is generated only if those defect occurrences are indicated by both region reports in the two different spaces. That type of report is generated by a logical AND operation that determines if the T-T" space reports a coordinate in region 520 AND the R-R" space also reports a coordinate in region 630. Positive verification of both occurrences then produces a final report that indicates the presence of that type of transmissivity defect.

Thus, the final defect detection and classification procedure is carried out by merging the various region reports. Some types of defects may be conditional on multiple reports, such as the transmissivity defect discussed above, while other types of defects may be unconditionally indicated by single individual reports. From a hyperspace perspective, some defects can be determined in two dimensional space (e.g. T-R, or T-T" or R-R" space individually, that is from a single report as described above), while others can only be determined in three dimensional space (e.g. T-R-T"). Others may require four dimensional space, or five dimensional space, etc.

Electronic subsystem 20 is thus programmed to perform the necessary combinations of logical operations in the required order to generate a final defect report that identifies the defects of interest from the collected region defect reports. The final defect report is generated by first combining all the conditional reports by AND operations in the proper sequence, and then ORing those results with the other reports with the final defect report thus indicating a defect if any of the individual region reports indicate a defect, by either conditional or unconditional detection (i.e. from two, three, four, five, . . . space in the hyperspace model), and provides a defect type code that indicates which regions from the defect region reports were responsible for determining the presence of the defect.

In practice, given the materials of current interest, the various defect types are detected by fusion of the analytic results obtained from the three individual detection spaces, which involve the four pixel observables T, R, T", and R", which have been discussed above as being plotted pairwise in three individual two-dimensional coordinate planes to simplify the initial consideration of the method of the second aspect of the present invention. In reality, the defect detection process of the second aspect of the present invention occurs within a four-dimensional observation hyperspace with coordinate axes T, R, T", and R", with the four observables from each pixel forming a four-component vector. Additionally, this hyperspace can be subdivided into various hyperdimensional classification regions as illustrated in FIGS. 20-22, and even T-R", R-T", and T"-R" spaces, if for some material/defect combination those spaces would also be of interest in the resolution of whether a particular type of defect is present that can not be determined from one or more of the previously discussed spaces. Since the nominal defect-free behavior of an inspected substrate will contain a high degree of correlation in this four dimensional hyperspace, the second aspect of the present invention takes advantage of this redundancy by analyzing the observables in pairs, projecting the observable four-vectors onto selected two-dimensional coordinate subplanes, essentially decomposing the four-dimensional observation space into three individual two-dimensional subspaces for simpler visualization, calculation and identification of defect types.

Thus, it is easy to visualize that alternate embodiments of the second aspect of the present invention might effectively utilize other possible combinations of the four observables for detection analysis, T versus R" for example. Furthermore, such alternate subspaces need not be limited to two-dimensional projections of the observables, and in principle may extend to utilization of the entire four-dimensional representation for detection analysis as inferentially discussed above.

Furthermore, other observables might be generated by performing alternative filtering operations on the measured T and R signals as represented by the block diagram of FIG. 24. For example, the measured T and R signals and additional high-order signals derived from the measured signals to create image maps. Thus, in addition to the second derivative functions as discussed above, larger convolution operators with unique coefficient values might also be used to produce other signals to analyze to more clearly reveal other characteristics of a substrate of interest. In general, given an arbitrary number of observables (e.g. derivatives of various levels, signal range limitations of which selected derivatives may be taken, integrations, or any other type of function that can be generated from the measured T and R signal values), they may be analyzed within an arbitrary number of subspaces of the observation space, of arbitrary dimensionality less than or equal to the number of observables (two to n dimensional space). As already discussed above, comprehensive defect detection using lower-dimensional subspaces of the observation space generally requires that all the information from all reporting subspaces be collected and merged for final evaluation.

FIG. 24, more specifically, illustrates a general case for performing M operations on the actual T signal 700 and N operations on the actual reflected signal 702 from the transmission and reflected pixel image map of the surface being inspected. Each of those various operations in the first tier of blocks are identified by a series of filters identified as $f_x(T)$ or $g_y(R)$. For the process described above, filters $f_1(T)$ 704 and $g_1(R)$ 706 are each all pass filters, and filters $f_2(T)$ 708 and $g_2(R)$ 710 are each second derivative filters to form the signals T" and R", respectively, from the input T and R signals.

The other filters that might be included in the first tier of operations are illustrated here as $f_M(T)$ 712 and $g_N(R)$ 714 which may perform another function on the input T and R signals to form other signals that would be useful to identify another feature of interest on substrate 14.

The second tier of operations in FIG. 24 is the combination of the various signals from the first tier filters in two dimensional space of each possible combination, or at least those of interest, of the signals from the first tier filters. For example, if $f_1(T)$ 704 and $g_1(R)$ 706 are each all pass filters, and filters $f_2(T)$ 708 and $g_2(R)$ 710 are each second derivative filters, then in block 716 the T-R space information would be collected, in block 718 the T-T" space information is collected, in block 720 the R-R" space information is collected, in block 722 the T-R" space information is collected, in block 724 the R-T" space information is collected, and in block 726 the T"-R" information is collected. The other blocks in this level illustrate the collection of other combinations of signals to present the values of those signals in the corresponding two dimensional space. The results of each of the blocks in the second tier are provided to the third tier which consists of a logical defect merge function 728. The logical defect merge function 728 could be implemented with a microprocessor programmed to identify values of the signal pairs in each of the blocks of the second tier that represent a particular defect, and then to prepare a comprehensive defect report of all of the defects that were revealed by each of the signal pairs of the various blocks in the second tier.

Computation of the Second Derivative

Although this transformation is not a point operation function, a local neighborhood of pixels adjacent to the pixel in question is the only requisite of image integrity for computation and analysis of the second derivative. All features of this aspect of the system involve the reduction of reference data to a coordinate-free statistical representation. The reference map does not contain information about the expected substrate behavior at any specific location, but rather represents the statistical behavior at some point on the substrate with the entire substrate, or region of interest of the substrate, being inspected.

This aspect of the system has no requirement for direct comparison between test images and reference images, whether from an adjacent identical lithographic pattern or CAD database, and hence an alignment system is still not required.

Prior to discussing the second derivative method in particular, attention is directed to FIG. 23a where a pixelized transmission value image of the region of interest of a substrate 14 is illustrated. For purposes of discussion the image is shown as a matrix of individual pixel transmission values, $t_{x,y}$, for an image that is n×m pixels in size. A pixelized reflection value image would be similar and of the same size for the same region of interest of substrate 14. Such a reflection value image can be visualized by replacing the variable "t" in FIG. 23a with an "r".

The purpose of the second derivative computation is to provide information about the proximity to an edge of a feature or defect. The second derivative computation is a linear convolution operation on the given image. At every pixel in the image (e.g. $t_{x,y}$ in FIG. 23a), a local rectangular neighborhood of pixels, with the current pixel at the center (e.g. for a 3×3 operation):

| $t_{x-1,y-1}$ | $t_{x-1,y}$ | $t_{x-1,y+1}$ |
| $t_{x,y-1}$ | $t_{x,y}$ | $t_{x,y+1}$ |
| $t_{x+1,y-1}$ | $t_{x+1,y}$ | $t_{x+1,y+1}$ | is input to a linear operation by a rectangular matrix, L, of the same size (3×3 in this example) to produce a single output value for the second derivative value of the central pixel ($t_{x,y} => t''_{x,y}$) at that point.

That convolution can be represented as follows:

[T"]=[L]∘[T]

Thus, the value of each element of the second derivative image as defined in FIG. 23b can be expressed mathematically as:

$$T''(x, y) = \sum_{ij}^{-1 \text{ to } l} L(ij)T(x-i, y-j)$$

In this operation, however, there is an erosion at the edges of the transmission pixel image in that the resulting T" image matrix as shown in FIG. 23b has no values in the outer most rows and columns around the edge of that image.

The selection of L for performing the second derivative function can take many forms. The values for L illustrated here is a Lambertian technique that is common in the art, and one that is symmetric in two dimensions since the transform here is being performed in two dimensions. L in this example has been selected to have a spectral response in the other domain that is as circularly symmetric as possible.

Thus, through this operation, the T=>T" and R=>R" transformations are performed. For purposes of illustration here, the second derivative of the T or R pixelized images is computed by approximating it with a high pass filter, L, or convolution matrix:

$$L = \begin{matrix} d & v & d \\ h & c & h \\ d & v & d \end{matrix}$$

where typical values are: c=0.1817536, d=0.01539003 and v=h=−0.0648287.

An alternate implementation to the convolution operation on digitized pixel data is to optically process the image using the well-known Fourier filtering techniques with coherent light to perform the high-pass filtering before the sampling process.

Methods of Reference Map Generation

As mentioned above, the T-R, T-T", and R-R" detection spaces are utilized to characterize the behavior of a substrate under inspection by bounding the non-defective regions in each detection space. In fact, the success of the current method rests on the ability to define the boundaries of the defect-free regions in the T-R, T-T" and RR" spaces. The definitions of those regions for each reference map are necessary for satisfactory defect detection; additionally, each reference map may contain defect classification zones which are adjustable as desired according to the response of the defects to the inspection process.

Experiments have shown that substrate characteristics vary sufficiently so that the defect-free boundaries have to be determined for each substrate in order to optimize the inspection sensitivity for that substrate. On the contrary, the defect classification regions are more generic to the inspection method than the substrate, and errors in classification have a lower cost value than errors in detection. Therefore, the classification zones will be adjusted less frequently in practice, and can be adjusted by heuristic and long-term statistical analysis of defect characteristics.

The purpose of this section is to explain how nominal non-defective substrate information is obtained and encoded in the detection space (i.e. experimental determination of shapes and tolerance regions of defect free zones in T-R, T-T" and R-R" spaces). Analytical methods for determining the defect-free region in the T-R reference map are described below with these methods carrying over to the determination of the defect-free boundaries for the T-T" and R-R" reference maps.

Generally, reference mapping can be regarded as a training process where the nominal behavior of the substrate type is observed by a representative sampling of a defect-free area of a selected number of substrates of the same type to account for production tolerances. It should be noted that reference curves can be developed using a single substrate, however, the use of several provides a better statistical average and the possibility of overcoming the inclusion of a defect on one of the sample substrates.

Thus, each substrate used for set-up of the system is sampled in the same area and the T, R, T", and R" signals measured at the sample points, and those signals are then plotted in detection space as a record of the sample population.

Filtering (described below) is then performed on this data record in order to approximate the true statistical behavior of defect-free pixels for the particular type of substrate used to develop the defect-free areas in each of the reference maps. Thus, this process creates a reference map with each point designated as defective or non-defective by a binary value. The reference map so developed may then be extended to other values and further encoded for defect classification purposes.

In particular, an area on the substrate with representative photolithographic patterns is chosen to serve as a typical reference sample for the substrates under inspection. This sample region can be chosen by an operator of the inspection system or automatically under control of the system computer. With either method of choosing the reference sample region for reference locus characterization, it is necessary to ensure, as much as possible, that the reference sample is free of defects. Once the reference samples are chosen, transmitted and reflected light images of the reference samples in the selected region are acquired.

At this point, a number of methods may be applied to obtain the defect-free region in each of the reference maps. Three of these methods are described below, each of which may be performed by automatic computation.

For example, a binary scatter plot of all pixels taken of the sample(s) may be generated in the T-R plane with every point in T-R space occupied by at least one sample pixel assigned a value of one. All remaining unoccupied points in the T-R plane are assigned zero values. Typically, most of the occupied points will be concentrated within a cluster in envelope 421 (FIG. 20) but there will also be some unoccupied points within that envelope and possibly some occupied points outside that envelope due to anomalies in the sample.

Next this binary scatter plot is operated on to generate a contiguous area within envelope 421 where all points have unitary value, surrounded by only zeros in the remainder of the T-R plane. To achieve this, standard binary morphological operations are performed, such as described on pp. 384-389 of a book entitled Fundamentals of Digital Image Operation, written by Anil K. Jain. (Prentice-Hall, Englewood Cliffs, N.J., 1989.)

Typically, a dilation operation might be applied first, using a symmetric kernel that is at least large enough to remove all the gaps that were present within the body of the sample cluster between the originally sized pixels. The result is a binary distribution which has been filled and expanded.

Similarly, an erosion operation using a symmetric kernel can be used to produce a reference envelope of the required size. Thus, inspection sensitivity is controlled by adjusting the size of the final reference envelope, and therefore the nature and size of the final operation.

Dilation of the envelope reduces sensitivity, while erosion has the opposite effect. In general, the final envelope should be larger than the sample cluster since the finite sample cluster only partially represents the statistical distribution of defect-free points.

For a more accurate representation of the sample data, a multi-valued histogram of the reference sample in T-R space might be preferred instead of a binary scatter plot. Using this approach an actual count is maintained for each coordinate within T-R space as the sample substrates are scanned to develop the defect-free region in T-R space. The resultant histogram can then be smoothed by application of an integrating filter, and converted to a binary-valued map by thresholding.

The advantage of the histogram approach is that T-R points are weighted by their frequency of occurrence, so that rarely occurring T-R points will not be weighted as heavily as frequent values during integration. Also, the adjusting of the final threshold controls eliminates anomalous, infrequently occurring, values from the final T-R reference map. Further, the width of the integrating filter also allows some sensitivity control.

Another technique of manipulating the sample histogram to define the defect-free locus is by multivalued morphology, as explained in a paper by Haralick et al: "Image Analysis Using Mathematical Morphology", IEEE Transactions on Pattern Analysis and Machine Intelligence, Vol PAMI-9, No. 4, July 1987. This processing approach is a multi-valued extension of the binary morphology already cited, defining dilation and erosion operations on functions with multi-valued range. This approach represents something of a hybrid of the previous two approaches, in that multi-valued dilations and erosions would be applied, in place of an integrating filter, to obtain a smoothed histogram, and a final threshold operation would reduce the mapping to a binary value.

As discussed above, a laser scanning system may be used to simultaneously generate transmitted and reflected light signal pairs, the method of inspection and defect classification of the second aspect of the present invention can be utilized with any image scanning process which is capable of generating synchronized transmitted and reflected light signal pairs.

Furthermore, this method of detection and classification can be utilized with any image scanning process which is capable of generating synchronized multiple light signals, generated by any number of light detectors placed in any direction about the substrate, which may be illuminated by any light source directed at any angle toward the substrate. As explained in the discussion of the detection space, the number and nature of the observables need not be restricted to T, R, T", and R", so long as there is sufficient correlation within the observables that a reference map can be generated to perform satisfactory detection and classification.

An alternate method for detecting and classifying defects is with neural network methods. For example, the detection spaces and reference maps developed by the processes discussed-above can be implemented as an input/output mapping with a three-layer backpropagation network (BPN) as described in pp. 89-126 in a book Neural Networks—Algorithms, Applications, and Programming Techniques by J. A. Freeman and D. M. Skapura, Addison-Wesley, Reading, Mass., 1991.

Figure 25:
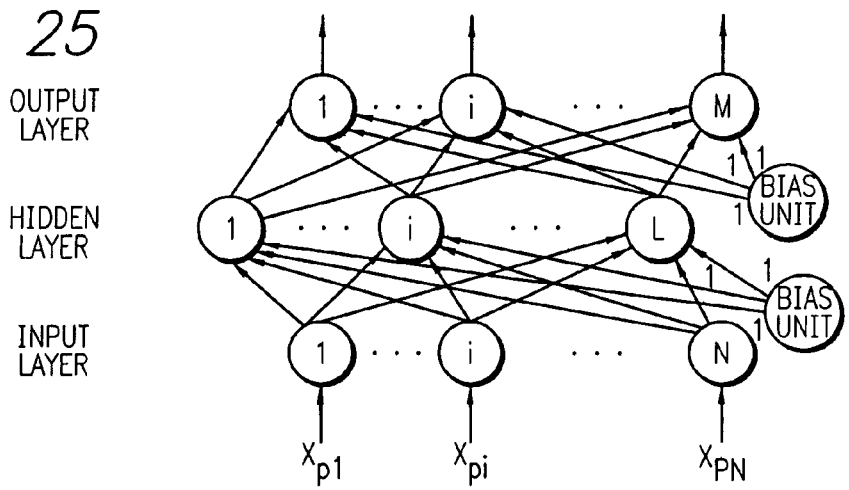
FIG. 25 is a typical representation of a BPN neural network.

For the neural network approach, requirements on the scanning system are the same as discussed above with the following modification. A typical BPN, illustrated in FIG. 25, is composed of three layers of neurons, an input layer, a hidden processing layer, and an output layer. Each neuron in the input layer receives an observable (e.g. a single pixel of the local rectangular neighborhood of pixels discussed above with respect to FIGS. 23a and 23b from both the T and R signals) as an input signal and passes it to the second, or hidden, layer; each neuron in the hidden layer receives all outputs from all neurons in the first layer and generates an independent output signal; and each neuron in the third layer receives all outputs from all neurons in the hidden layer and generates an independent output signal. Thus, each neuron creates an output signal based on a weighted linear activation function of the combined inputs from all of the nodes in the previous layer. Each of those weighted linear activation function having been determined during the learning phase through variations in the individual biasing of each node of the hidden and output layers. The biasing functions can either be calculated and then applied to the respective biasing unit, or the learning can be performed in a dynamic environment, even an on-going procedure in some applications where not all possible outcomes are known at the outset. Additional discussion of the learning phase is presented below to further illustrate this process.

In operation, even though each node in the hidden and output layers receives the output signal from each node of the previous layer, not all of those signals are necessarily used in the performance of the particular function of that particular node. The interconnection of all nodes in the previous layer to every node in the next layer is the result of the standardization used in the production of the BPN since the effect of various signals can effectively be ignored at those nodes where that signal is not of interest. That is, the biasing of each hidden node can be adjusted to generate an output signal from that node that is an approximation of the values, for example, in the T-T" space of the second aspect of the present invention while ignoring the R and R" signals from the input layer nodes.

Thus such a BPN might have four input neurons for the four observables T, R, T", and R", a hidden layer which measures many different activation potentials corresponding to different correlations in the data, and an output layer which generates a set of membership values, each output neuron node assigned a membership value for a specific defect class. The final evaluation might be determined by the class with the maximum membership value. This implementation is actually an alternative method for determining the same input-output relationship, referred to as the reference map, which is a generic aspect of the present invention. In fact, the input layer corresponds to the coordinates of the detection space, the output signals correspond to the defect class assignment for a given input signal, and the hidden layer corresponds to an optimal analytical or logical procedure for assigning a class to each input, as embodied in the reference map.

The backpropagation feature of such a network is used to train the weights in the hidden and output layers so that the desired mapping is achieved and errors are minimized. The training procedure described previously can be easily adapted to this implementation by feeding the sample data through the backpropagation procedure and adjusting the weights to match desired outputs to the inputs. Furthermore, backpropagation allows the BPN to continue training during use whenever a secondary defect verification procedure is required.

Another variation to this approach applies where the network also performs the filtering on the T and R signals, so that the input layer consists of 18 input neurons, accepting the 9 transmitted values and the 9 reflected values contained within a 3 by 3 neighborhood of pixels.

One particular aspect of the present invention is to extend the application of transmitted and reflected imaging to photomask pattern inspection using die-to-die (DD) or die-to-database (DDB) comparison techniques. Comparative pattern inspection algorithms typically locate defects that produce significant differences between an optical image of the specimen and a reference image. The reference image may be from a previous sample stored and recalled from memory (DD), or derived from the photomask design database (DDB).

Figure 27A:
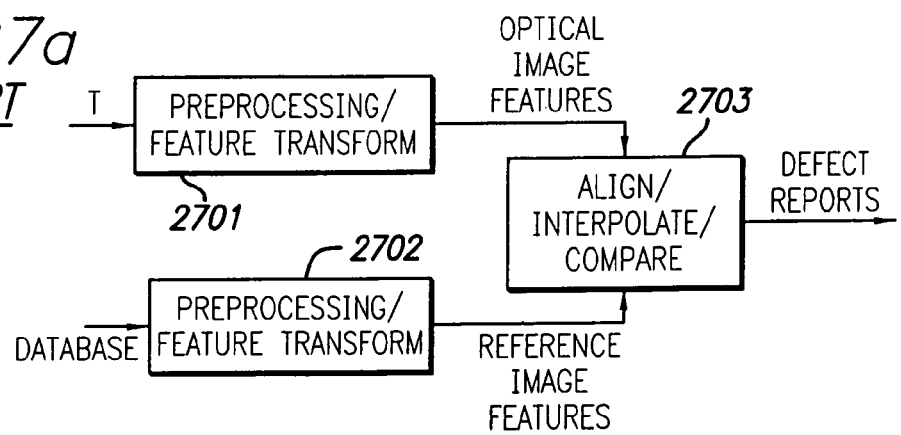
FIG. 27a is an illustration of the prior system for detecting defects.

The previous die-to-database system is illustrated in FIG. 27a. The system of FIG. 27a receives transmitted greyscale data and performs a preprocessing transformation in block 2701. The system also performs a similar preprocessing transformation on the reference database image in block 2702. The preprocessing transformation converts greyscale data to image features which facilitate the defect detection process. The feature transform may apply any of a variety of linear or nonlinear operations on local or neighborhood image domains to obtain features having useful attributes. The system then performs all subsequent functions on the optical and reference image features, including an align/interpolate/compare algorithm to determine defects, as shown in block 2703. Block 2703 performs an alignment of the optical and reference image features, interpolates image points between recognizable optical and reference image features, and compares the optical and reference features. Interpolation may be required due to offsets in data sampling coordinates, which can produce difference errors exceeding the defect threshold. Based on this align, interpolate, and compare algorithm, defects may be determined and addressed. Note that neither the reflected signal nor image is used in any block of this configuration.

In evaluating the performance and capabilities of pattern inspection systems in connection with various sample or pattern types, the foregoing methods for detection of particles and contamination, using transmitted and reflected images, were sensitive to phase transitions and defects found on Alternating Phase Shift Masks (APSMs). These mask types are physically similar to common quartz and chrome photomasks, except where thickness transitions are etched in the clear material in APSM photomasks to induce phase shifting between adjacent regions during photolithography. Under inspection, these phase transitions produce unique variations in the T-R, T-T" and R-R" detection spaces defined above. However, phase defects, which are unwanted transitions accidentally created by phase etch process errors, produce similar variations within the same detection spaces. Thus the application of T-R, T-T" and R-R" detection space operations can be applied to transmitted and reflected APSM images to detect any phase features in the photomask, but these operations are not sufficient to determine whether a detected phase feature is a defect or a non-defective design transition. However phase defects can be recognized by the system if all detected phase features are properly compared and contrasted to reference photomask image data. Detected phase features can be evaluated by die-to-die or die-to-database comparison to discriminate between phase defects and non-defective design features.

As noted above, APSM photomasks include phase shifting features resulting from depth differences within the glass or quartz portions of the specimen. The presence of edges due to depth differences can produce scattering or other forms of image interference when the specimen is exposed to light. Due to these scattering and interference effects, APSM phase transitions can produce transmitted and reflected image variations similar to those shown in FIG. 28 during inspection. Specifically, phase transitions on the clear substrate can produce signals similar to the blips 371, 375 and 377 shown in FIG. 18. Phase defects produced by errors during the etch process can produce similar signals. The previous system identifies phase features using the image filters and reference maps shown in FIGS. 19-24 in the same way particles can be identified as defects. However, these operations are insufficient to determine whether a detected phase feature is actually a design transition or a defect. Therefore the previous system simply flags any detected phase feature as a defect and requires further processing or interpretation to properly verify the feature as defective or non-defective.

The present system also identifies these phase features using the image filters and reference maps shown in FIGS. 19-24. Furthermore, the present system recognizes that a detected phase feature may not actually be a defect. The system interprets outputs of the image operations in FIGS. 19-24 are to be phase feature indicators rather than defect indicators, corresponding to the existence of a phase feature rather than a definite defect. To determine whether the feature corresponds to an actual defect, the system evaluates the output both with respect to the reference image and by die-to-die or die to database comparison. If the feature is not matched in the reference image, then the algorithm indicats the existence of a defect.

The present system, the system recognizes that a phase transition may not actually be a defect. The output of the image operations in FIGS. 19-24 are evaluated with respect to the reference image and interpreted to be phase transition indicators rather than defect indicators. In this embodiment the output of the system corresponds to the existence of a feature rather than a definite defect. To determine whether the feature corresponds to an actual defect, the output is evaluated by die-to-die or die to database comparison. If the feature is not matched in the reference image, then the algorithm indicates the existence of a defect.

Figure 27B:
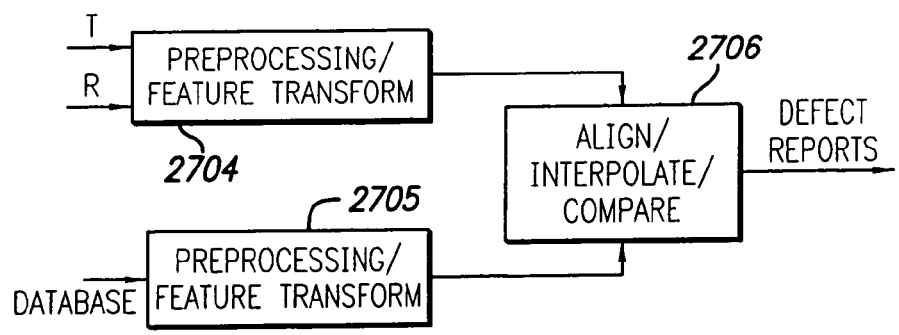
FIG. 27b illustrates the application of the image processing operations shown in FIGS. 19-24 on both transmitted and reflected images to produce optical image features.

The present system detects APSM phase defects using transmitted and reflected image acquisition and processing. For this realization, the preprocessing block 2704 in FIG. 27b applies the image processing operations shown in FIGS. 19-24 on both transmitted and reflected images to produce optical image features. Features having recognizable phase transition characteristics, such as a known phase shift based on known photomask characteristics, are flagged. It is generally recognized that particular APSM specimens may have 45, 60, or 90 degree phase shifts, or other known angular shifts, and these shifts may be recognized as known characteristics and flagged accordingly. These flagged features are encoded to indicate whether or not a phase transition was detected and passed to subsequent processing locks.

Preprocessing block 2705 also applies a feature transform operation to the reference or database image to produce reference phase features. The feature transform operation takes known information into account, such as phase transition levels for the specimen, and transitions recognizable features into data representations thereof. The system then performs all subsequent functions on the optical and reference features including an align/interpolate/compare algorithm for detection of phase defects. This subsequent processing is performed by the system in block 2706.

Significant benefits exist for the present inspection system over the use of transmitted images alone. In general, the use of both transmitted and reflected images produces a higher probability of phase transition detection than with the use of transmitted imaging alone. Use of both images also reduces the probability of false phase transition detection due to systematic noise. Also, in the case of APSM specimen inspection, the transmitted and reflected image components are phase shifted by different intervals as a result of differences in optical data length. In some cases, depending on the actual phase shift induced on the illuminating light, a reflected image may produce a stronger signal-to-noise ratio than a transmitted image on APSM phase transitions.

As noted, one particular aspect of the current invention is to extend the application of transmitted and reflected imaging to photomask pattern inspection with die-to-die or die-to-database comparison methods.

In evaluating the performance and capabilities of pattern inspection systems with various sample or pattern types, it became apparent that transmitted optical image characteristics related to EPSM were not in conformance with other specimen types. In particular, the normalized transmitted scan plot shown in FIG. 17 is altered when inspecting an EPSM as a result of the phase shifting properties of the mask. Furthermore, interference due to phase shifting can reduce the transmitted image response associated with small defects in the substrate, such as pinholes. Reflected images can be used to correct or enhance transmitted image deficiencies and abnormalities associated with patterns and defects.

Figure 26:
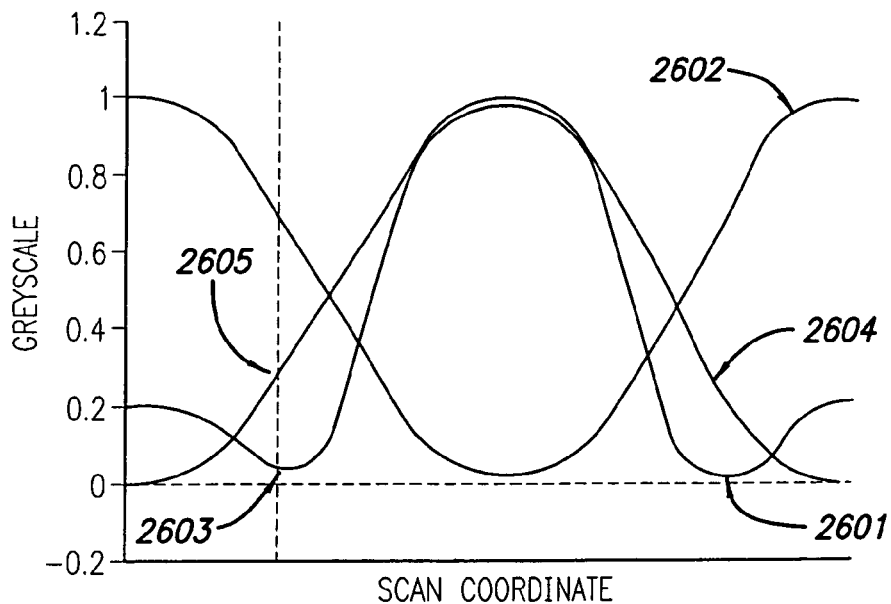
FIG. 26 shows a graph of the relationship between transmitted and reflected light signal pairs when inspecting typical embedded phase shift mask.

For the plot shown in FIG. 17, each value on the greyscale axis is associated with a single point on the scan axis. This uniqueness between greyscale value and scan coordinate is no longer valid when scanning, for example, an EPSM sample. As shown in FIG. 26, the greyscale plot of normalized transmitted and reflected light signals 2602 and 2604/2605, respectively, differs for a scan across an EPSM substrate as shown by the line including anomalies 2601 and 2603 and varies such that the transmitted greyscale values are not uniquely associated with a single coordinate on the scan axis, or equivalently, on the inspected substrate. This irregularity shown by anomalies 2601 and 2603 occurs because the dark EPSM material is not completely opaque and passes light through the specimen. It has been noted that for dark and clear materials, destructive interference occurs at pattern edges producing a dark fringe in the transmitted image scan. Away from edges the scan transitions to the typical flat field response.

Therefore, a transmitted image scan across the substrate produces a greyscale plot as shown by the line including anomalies 2601 and 2603 in FIG. 26, and such a plot may yield a dark fringe at the pattern edge that creates an ambiguity between greyscale values and scan coordinates, unlike the plots of FIGS. 17 and 18. This ambiguity is detrimental to the defect detection process, producing errors during preprocessing, alignment, interpolation, and comparison.

Figure 28:
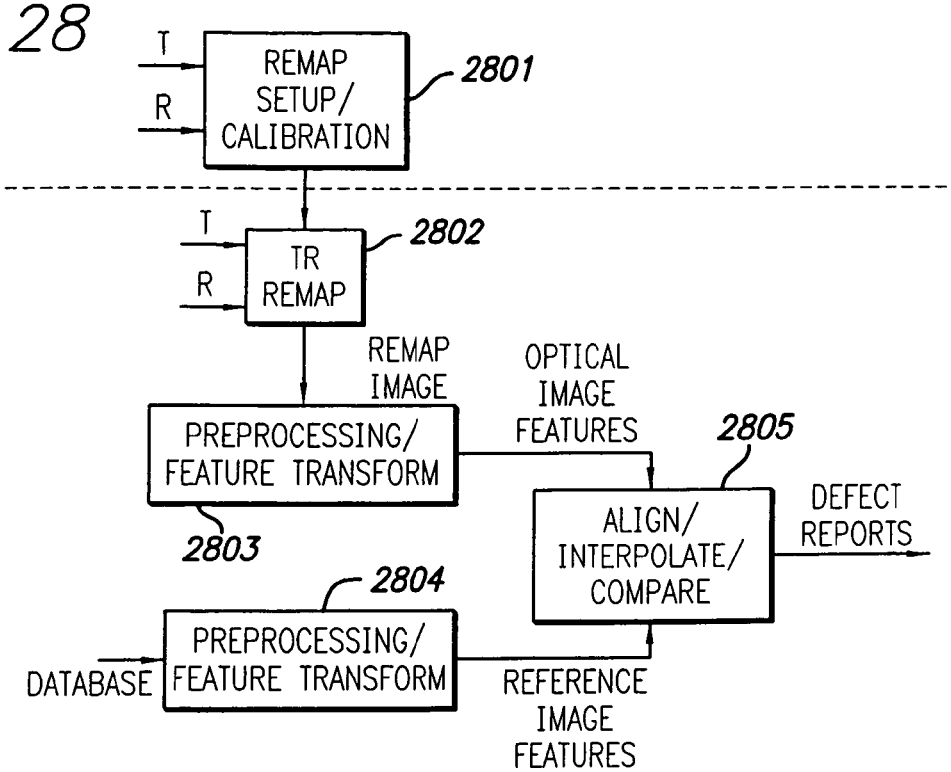
FIG. 28 presents the current system for performing inspection of an embedded phase shift mask using a pattern inspection algorithm.

The system addresses this transmission interference problem when performing the inspection and is illustrated in FIG. 28. Transmitted and reflected light intensities are passed through fiber optic channels to minimize propagation offsets and then sampled simultaneously. The system samples both transmitted and reflected images and passes them to remapping block 2801, which remaps each T-R sample to a single greyscale value, converting the two transmitted and reflected images into a single image. The system performs a transmitted and reflected remapping in block 2802, using data from block 2801 and producing a remapped image. Block 2803 preprocesses and performs feature transformation on the remapped image. The result produced by block 2803 is a set of optical image features. Block 2804 performs the preprocessing and feature transform on database information to produce reference image features. The system then performs an align/interpolate/compare algorithm on the optical image features and the reference image features to determine defects, as shown by block 2805.

Figure 29:
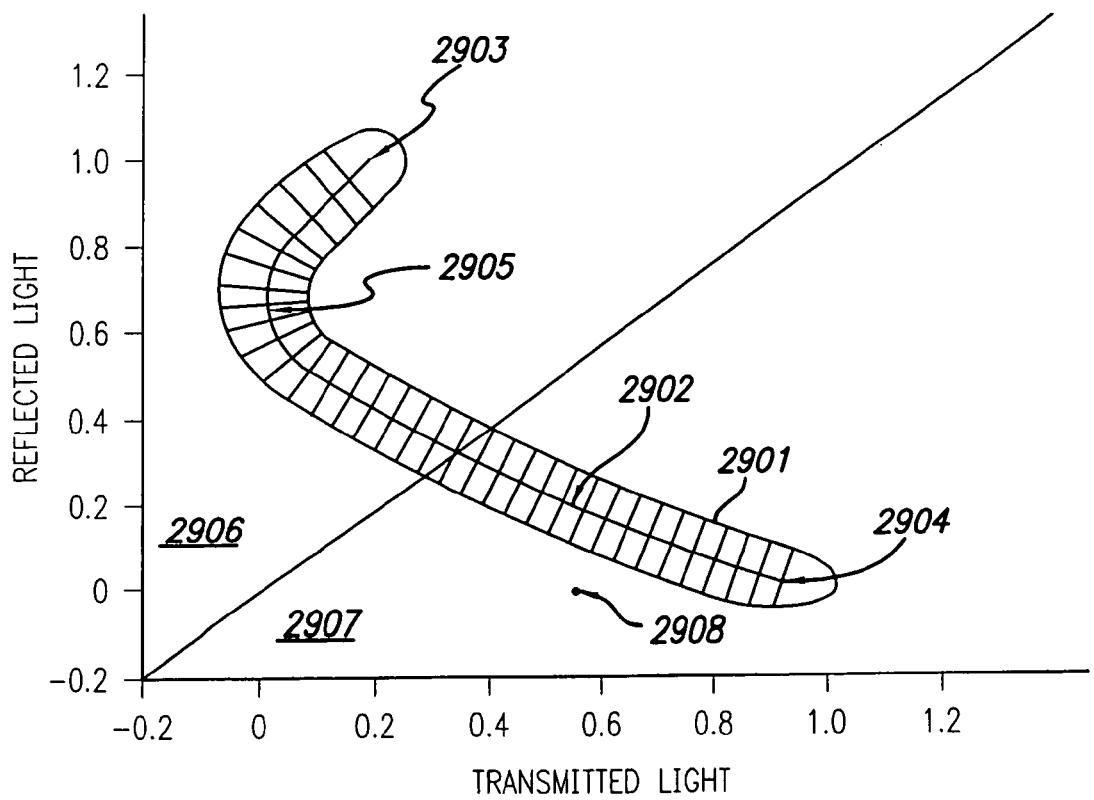
FIG. 29 represents a T-R curve for the present system.

The remap function is designed to produce images with no dark fringe near edges. The remap removes the fringe by reference to the reflected greyscale data, which is not altered by transmissive phase-shifting and is unambiguous in the scan region coincidental with the transmitted fringe, as shown in FIG. 26. While each point in the scan may not produce a unique transmitted greyscale value, each point in the scan does produce a unique point in the TR plane. The entire scan produces a set of points on a curve in TR-space as in FIG. 29, which represents the correlation between transmitted and reflected values on the substrate. A unique remap value can be assigned to every point on the curve, and the remap will be unique for every point on the scan axis, containing no fringes.

The system performs a pattern inspection algorithm on the remapped image to determine defects at and around the edges of the specimen pattern. By remapping the transmitted and reflected images into a single image, the processing requirements for preprocessing, alignment, interpolation, and comparison need not be duplicated for both images.

Further, in phase shift masks, a common problem is that a pinhole or phase variation may occur in the mask, which can be undetectable using transmitted light alone. In transmitted light, the modulation due to the pinhole may be very small due to destructive interference. Reflected light may, under some circumstances, produce a stronger signal than transmitted light. By including the signal from reflected light, the remap tends to have increased variation and detectability resulting from the flaw. Sometimes this effect breaks the T-R correlation, and thus becomes distinguishable by separating from the T-R plot, as in point 2908 of FIG. 29.

The remap function is determined before inspection during a calibration procedure by evaluating samples of representative transmitted and reflected images. The calibration can be performed by various methods, where the common objective is to analyze the correlation between transmitted and reflected values and assign an appropriate relationship between transmitted and reflected input values and remap output values. For any method, remap calibration must function effectively in the presence of greyscale measurement noise.

For example, one calibration method identifies pattern edges within the sample images and constructs mean transmitted and reflected scan profiles on a high-resolution grid along the scan axis. The remap scan profile is also defined on the scan axis and directly assigned at each point to the mean local transmitted and reflected values.

Another calibration method prepares a histogram in TR space representing the distribution of transmitted and reflected image values on the sample. The distribution scatters about a curve in the TR plane that traces the mean correlation between transmitted and reflected values as the scan transitions across pattern edges. Density analysis can be applied to the histogram to construct edge profiles and a TR correlation curve, and assign remap values in TR space.

A common step in TR remap calibration is to determine a model for the mean correlation curve in TR space and parameterize the curve with remap values. FIG. 26 shows the transmitted and reflected image profiles for a scan across a simple photomask pattern consisting of a single dark line. The mean correlation between transmitted and reflected image values is represented by curve 2902 in FIG. 29 Every coordinate on the scan axis in FIG. 26 corresponds to a particular point on curve 2902 in FIG. 29. As the scan transitions across the pattern in FIG. 26, the mean transmitted and reflected image values vary according to the mean correlation curve between endpoints 2903 and 2904 in FIG. 29.

The remap function is defined by scan profile 2604 in FIG. 26. For each point on the scan axis in FIG. 26, the transmitted, reflected, and remap values are uniquely correlated, providing a unique remap value for each point on curve 2902 in FIG. 29. The variation of the remap function is represented by parametric increments along curve 2902. In particular, the minimum remap value occurs at endpoint 2903, and the maximum remap occurs at endpoint 2904. At point 2905, which corresponds to point 2603 of FIG. 26, the remap value is equal to the remap value 2605 at the same scan coordinate associated with point 2603.

To allow for noise fluctuations, points off the mean correlation curve may be parameterized by selecting a point on the curve by minimum-distance rule. For contamination detection, TR space may be further divided by boundary 2901 enclosing the mean correlation curve. Points outside boundary 2901 may be remapped by maximum distance rule to increase the variation of contrast of dust and contaminants. The maximum distance rule splits the region exterior to boundary 2901 into two regions 2906 and 2907. After the entire TR plane is completely parameterized, the remap function is then stored into remapping block 2801 for reference during inspection.

Subsequent to the initial calibration procedure, the system scans the desired specimen to inspect it for defects. As with the calibration procedure, transmitted and reflected light intensities are passed through fiber optic channels to minimize propagation offsets and then sampled simultaneously. The system samples both transmitted and reflected images and passes them to remapping block 2801, which remaps each T-R sample to a single greyscale value, converting the two transmitted and reflected images into a single image. The system performs a pattern inspection algorithm on the remapped image to determine defects at and around the edges of the specimen pattern. Errors in preprocessing, alignment, interpolation, and comparison stages of the defect detection algorithm are reduced by removal of the fringe, enhancing the performance of the mask inspection. Furthermore, by selective dependence on both T&R image sources, the remap function can pass information from either image to the inspection algorithm for processing and algorithm for processing and defect detection, without duplicating the processing requirements for preprocessing, alignment, interpolation, and comparison for both images.

Reflected image data can be referenced to correct or enhance transmitted image deficiencies and abnormalities associated with, for example, EPSM patterns and defects, providing other possible benefits for EPSM inspection performance by remapping.

For example, interference due to phase-shifting can reduce the transmitted image response associated with small defects in the substrate, such as pinholes and phase variations, and such a defect may undetectable with transmitted imaging alone. However, the reflected image variation associated with the pinhole may be sufficient for detection, so that the defect may be detectable with variations from both transmitted and reflected images transferred into the remap.

Other defects such as particles, films, and contaminants may break the correlation between transmitted and reflected values sufficiently to fall outside an envelope of probable TR values on the substrate. These defects may be assigned remap values from the most distant neighbor on the remap curve to enhance their contrast in the remapped image.

TR remap may thus be applied with systems incorporating die-to-die or die-to-database comparison, or with comparison-independent systems which inspect for particles, films; and contaminants. Extensions to the TR remap function are possible using the present invention. For example, the system may include filter networks as in FIG. 24 or neural networks as in FIG. 25. These networks may operate on transmitted and reflected image data to produce enhancements to remap image characteristics and improve defect detection performance. One example is where both images may be independently transformed into features before being remapped into a single feature image. Another example is where both images are independently passed through separate preprocessing, alignment, interpolation, and comparison operations, producing two defect images which are then remapped into a single image.

While the system described herein is particularly useful in scanning EPSM and APSM, it is to be understood that the methods and information may be equally applicable and beneficial when scanning other types of masks, including chrome masks, and other wafer and reticle specimens. The procedures and structures used herein may therefore be beneficial in various scanning environments.

Advanced Phase Shift

In addition to EPSM and APSM capabilities, the present system has the ability to combine transmitted and reflected light and intelligently examine the results based on known defect patterns to detect additional anomalies present on the mask. The system employs an Advanced Phase Shift or APS method or algorithm to improve the system's ability to detect mask defects.

An example of a defect that is difficult to detect using transmitted light is a 90 degree phase bump in a 180 degree shifter area. The difference in the phase defect signal between transmitted and reflected light signals results from a difference in the amount of phase shift affecting the two illumination modes. For the transmitted light signal, the phase shift angle can be calculated from the following equation:

$$\Phi_t = (2\pi D(n-1))/\lambda$$

For the reflected light signal, the phase shift angle can be calculated from the equation:

$$\Phi_r = 4\pi D/\lambda$$

where $\Phi_t$ is the phase shift angle of the transmitted light signal (in radians), $\Phi_r$ is the phase shift angle of the reflected light signal (in radians), D is the physical shifter depth in the same units as the wavelength, $\pi$ is the refractive index of the shifter material, and $\lambda$ is the wavelength of illumination. Solving the two equations for D and setting the results equal, the relationship between phase shift angles is as follows:

$$\Phi_r = 2\Phi_t/(n-1)$$

Assuming the refractive index of phase shifter material is approximately 1.5, the reflected light phase shift angle is approximately 4 times the transmitted light phase shift angle. An assumption of 1.5 for the refractive index of the shifter material is approximately equal to the index of refraction at UV wavelengths of fused silica used for reticle substrates.

The maximum phase defect signal occurs at odd multiples of 180 degree phase shifts. Typical inspection system illumination wavelengths are on the order of 364 nm, such as for the KLA-Tencor 365UV-HR. A 364 nm wavelength is longer than that used for DUV lithography, and thus phase defects have proportionately decreased phase shifts and a decreased transmitted light signal for phase defects less than or equal to 180 degrees. In 248 nm DUV lithography, the phased shift is decreased by a factor of approximately 0.68 at the inspection wavelength. The reflected light signal exhibits a phase shift of approximately 2.73 at the inspection wavelength.

The use of reflected light in combination with transmitted light can improve detection of phase defects. The difficulty with using reflected light is managing image artifacts, such as the bright chrome halos resulting from the removal of the antireflective chrome layer during quartz etching of phase shifters. Bright chrome halos may have variable widths resulting from second write level registration tolerances with intra-plate variations. These variations are not observable when solely using transmitted light inspection techniques.

Several transmitted and reflected inspection implementations are possible including independent inspections using either illumination mode. As noted however, neither light mode may be ideal for phase-shift mask inspection. In transmitted mode, the light signal from phase defects may not be sufficiently strong for detection. In reflected mode, a light signal may contain bright chrome halo artifacts surrounding the etched quartz shifters, which can contribute to defect detection errors from the system. To combine the benefits from both image sources, simultaneous transmitted and reflected (T&R) light signals are input to a lookup table (LUT), known as TR Map, which outputs an enhanced, remapped image signal S=S(T,R), which is a function of both transmitted and reflected inputs.

The remapped image S=S(T,R) is operated upon by an inspection algorithm to search for defects. The remap operation controls and transforms the flow of transmitted and reflected image information into the inspection algorithm, and allows the inspection algorithm to view selected variations from both inputs without modification or duplication of processing requirements within the inspection algorithm itself.

Figure 30:
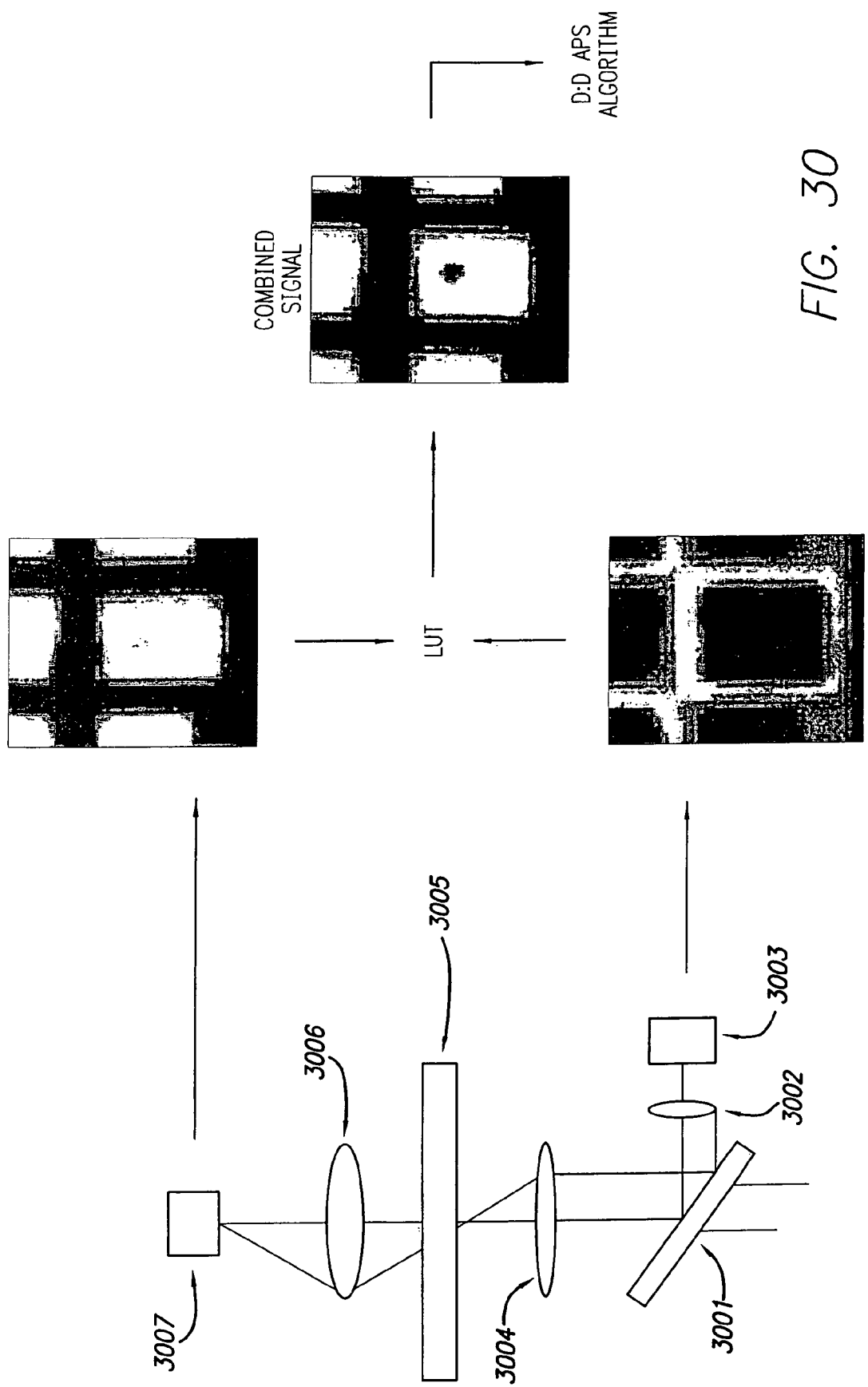
FIG. 30 illustrates a simplified version of the system incorporating the advanced phase shift (APS) method or algorithm.
Figure 31:
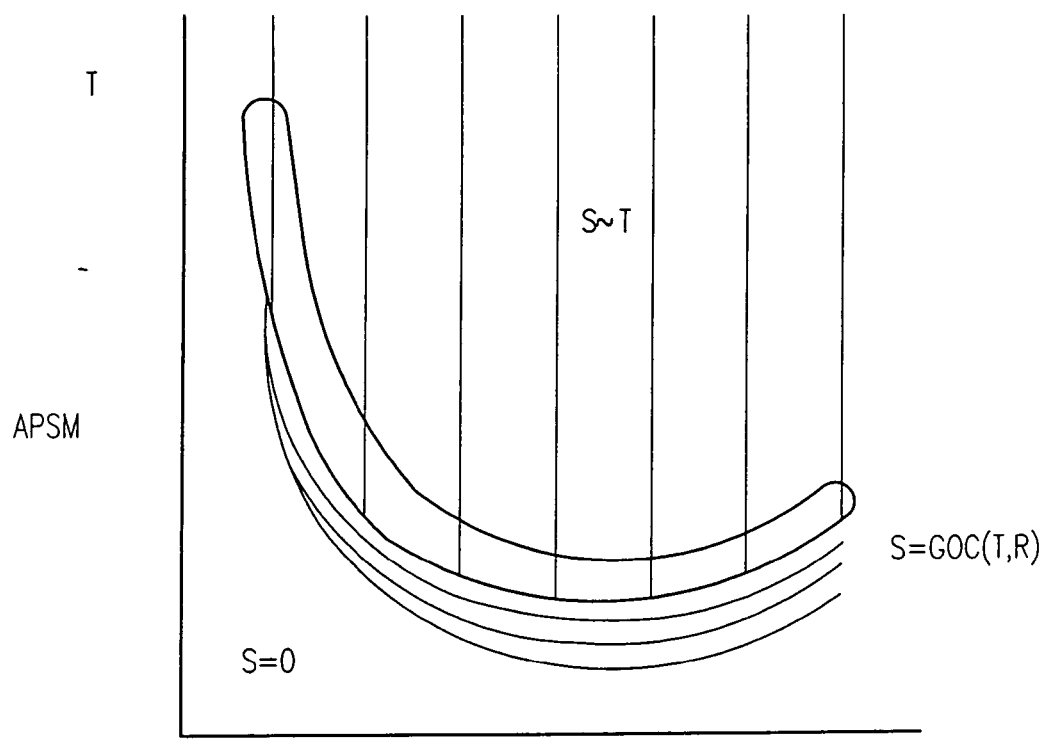
FIG. 31 is a diagram of the APSM species based on transmitted (T) and reflected (R) light received.
Figure 32:
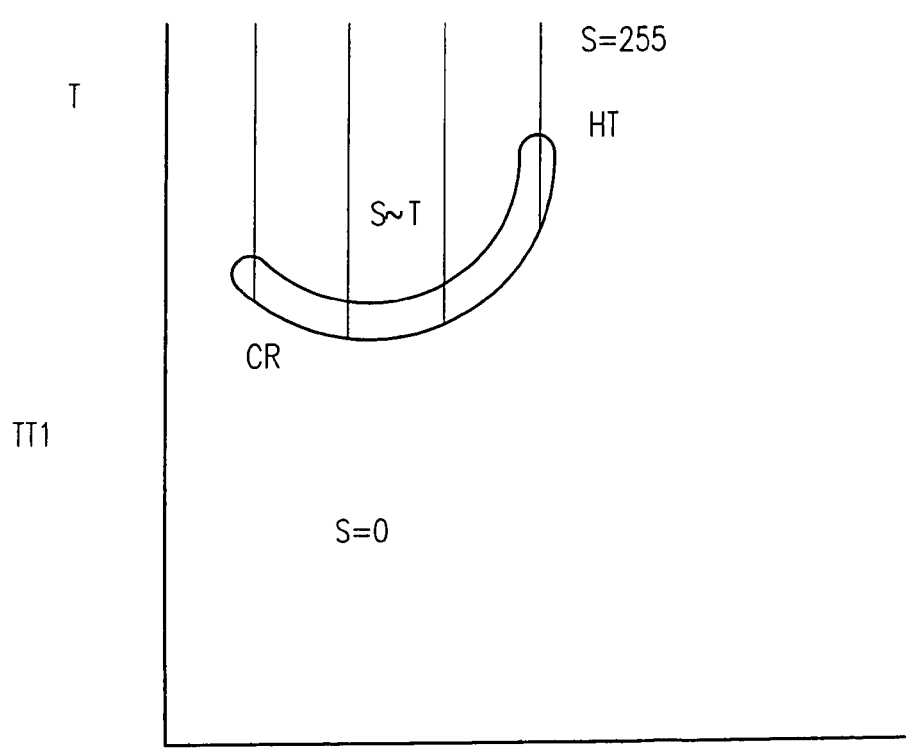
FIG. 32 is a diagram of the TT1 species based on transmitted (T) and reflected (R) light received.
Figure 33:
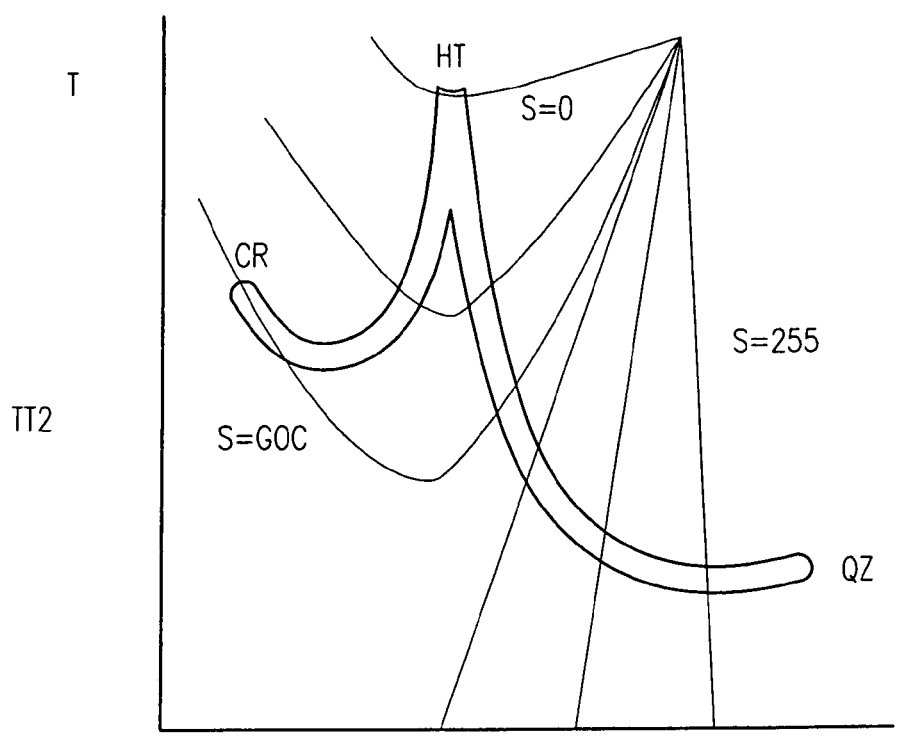
FIG. 33 is a diagram of the TT2 species based on transmitted (T) and reflected (R) light received.
Figure 34:
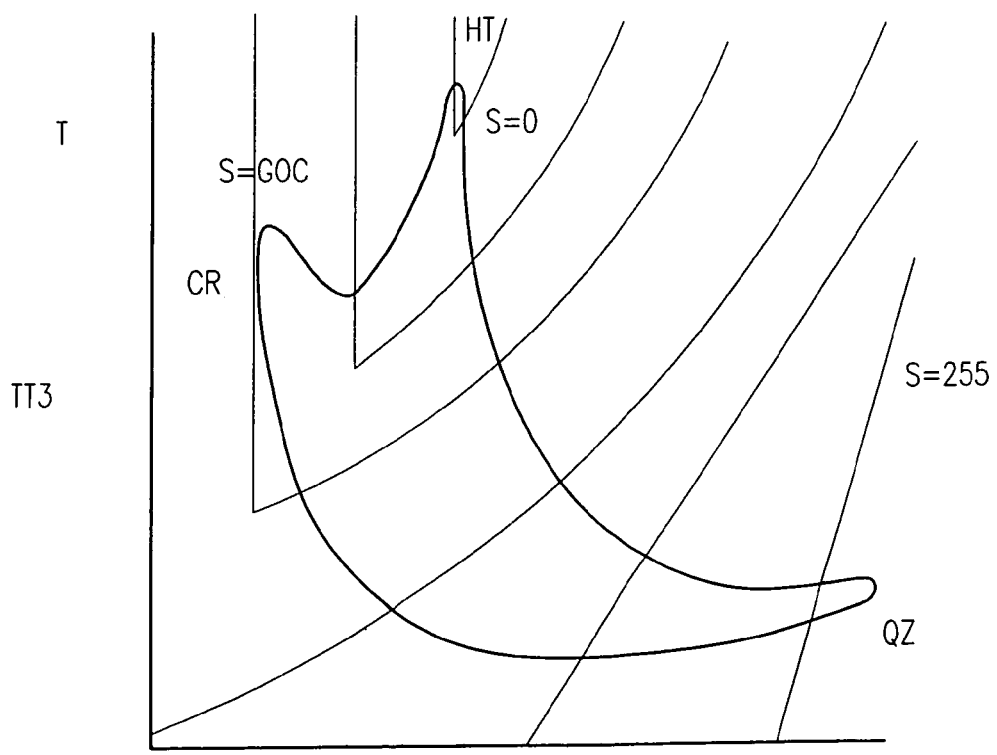
FIG. 34 is a diagram of the TT3 species based on transmitted (T) and reflected (R) light received.
Figure 35:
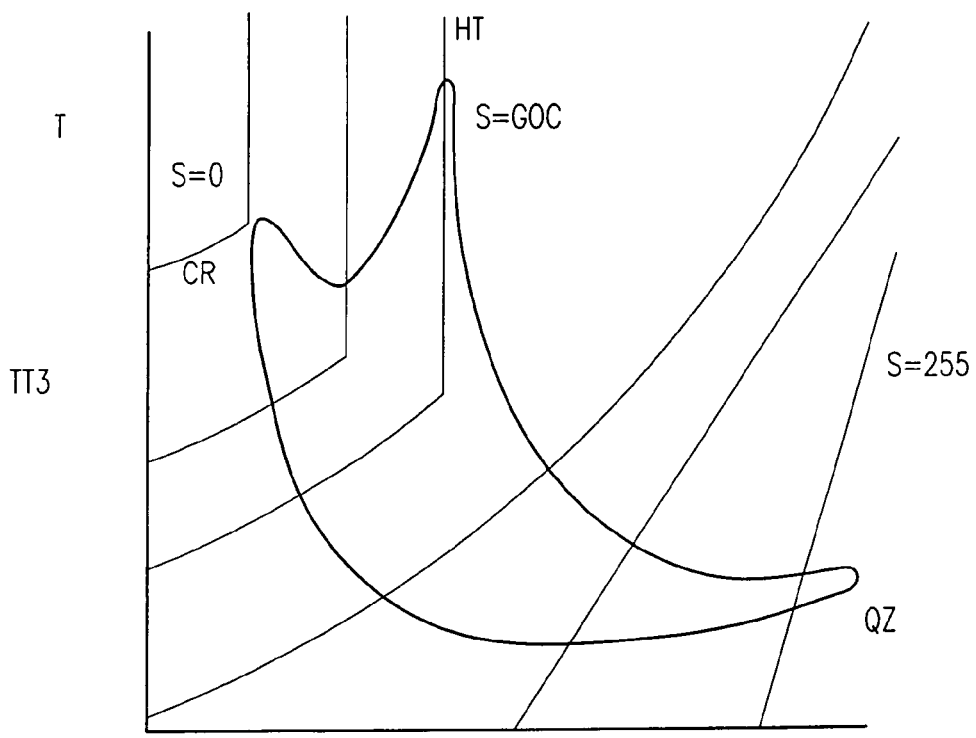
FIG. 35 is an alternate diagram of the TT3 species based on transmitted (T) and reflected (R) light received.

The Advanced Phase Shift or APS algorithm can apply the TR Map function to either die-to-die or die-to-database inspection modes. In die-to-die inspection mode, two or more nominally identical die are compared, and defects are indicated by differences between the die. A side view of a simplified representation of the system is presented in FIG. 30. From FIG. 30, a scanning laser beam inputs light energy to the system by directing light energy to mask 3001. Reflected light energy is directed to lens 3002 and reflected light sensor 3003.

Transmitted light passes to lens 3004, reticle 3005, lens 3006, and is received by transmitted light sensor 3007. The transmitted light image received by the transmitted light sensor 3007 and the reflected light image received by the reflected light sensor 3003 are combined using a LUT and the combined signal is compared using the die to die pattern APS algorithm.

In preparation for inspection, the system initially performs a light calibration function which captures T and R images with image rotation applied and measures the extreme values from both T and R channels. The system adjusts gains and offsets in both channels until the light measurements match predetermined target and tolerance values.

After light calibration, the system performs a TR Map Calibration procedure to determine the TR Map function $S=S(T,R)$. Again the system captures T and R images with image rotation applied. (T,R) greyscale statistics are analyzed in the (T,R) domain to derive TR Map. After calibration, the system loads the TR Map function into a lookup table at the input to the inspection algorithm and inspects the mask. By enabling the system to inspect the remapped image $S=S(T,R)$, TR Map broadly expands the inspection application capabilities of the system with the simple addition of a lookup table at the input to the inspection algorithm.

As one example, TR Map can be applied to inspection of one type of phase-shift photomask commonly known as a three-tone mask, composed of quartz, chrome, and half-tone (embedded attenuating) phase-shift material. Three-tone masks introduce complex multi-range transmitted and reflected pattern signals, which may be considered expected received transmitted/reflected signals, which can cause algorithms designed for simple mask inspection to produce unwanted defect detection errors. Combination of both transmitted and reflected signals by TR Map can resolve many of these signal complexities, by transforming or renormalizing different input greyscale ranges to a single common output range. For inspection of three-tone masks, the benefits of TR Map to the inspection system include the ability to detect defects in either transmitted or reflected light, the ability to remove edge fringes and other image anomalies associated with embedded phase-shift materials, and the ability to simplify complex inputs for processing by an inspection algorithm.

As another example, low contrast patterns which fail to meet standard light calibration objectives can be renormalized by TR Map operations to restore full greyscale range. This can have special significance for particular types of inspections on low contrast patterns such as halftone/chrome patterns, or ADI (After Development inspection) patterns, where the patterns may include photoresist in addition to chrome and/or quartz.

Furthermore, TR Map can be designed to enhance pattern inspection per application by remapping T&R greyscale values on certain photomask features. For APSM inspection, TR Map can produce remapped phase feature signals on quartz known as Grey-on-Quartz (GOQ) signals. One major application for GOQ is the amplification of phase defect signals by renormalizing their reflected light components. For three-tone mask inspection, TR Map can produce remapped chrome feature signals on quartz known as Grey-on-Chrome (GOC) signals. One major application for GOC is the simultaneous inspection of all three pattern materials on a three-tone mask: chrome (CR), quartz (QZ), and half-tone (HT) phase-shift material.

Each TR Map species has a unique set of calibration parameters. Each species defines a unique mathematical method for generating the TR Map function $S=S(T,R)$. Typically, S may generally be any analytical or mathematical model of a surface over a two-dimensional domain $S=S(T,R)$ For example, S may be defined by any combination of analytical, morphological, or statistical transformations or filtering operations performed on the (T,R) sample histogram defined earlier. In the following description of various TR Map species and calibration methods, the term "slug" refers to a histogram, in (T,R) space, of pattern signal data gathered by the system, filled and smoothed by filtering operations. Typically each species is designed with a set of variable parameters to permit a controllable range of output responses to input variations. Different applications within a species may require different optimal parameter values to be set based on other inspection conditions.

TR_Map_APSM: Used for inspection of alternating PSM, both dark-field and bright-field. Above the TR slug, the TR_Map_APSM depends on transmitted light only, to be blind to reflected signals and chrome halo variations. The transmitted input can be scaled or shifted if necessary by a set of polynomial coefficients. This can be useful on certain APSMs having weak image modulation due to deep quartz trenches.

Below the TR slug, APSM amplifies reflected variations on quartz for high sensitivity on phase edges and defects. This amplification is referred as Grey-on-Quartz (GOQ), and the TR subspace where it applies is referred to as the GOQ domain. Here the remap depends on both transmitted and reflected light, and the rate of GOQ variation on reflected light can be controlled by a set of polynomial coefficients.

TR_Map_TT1: Used for inspection of low-contrast HT/CR patterns. TT1 is a variation of APSM adapted for inspection of HT/CR patterns only. TT1 renormalizes transmitted greyscale to an optimal range on HT/CR patterns for maximum defect sensitivity. TT1 renormalization is controlled by a set of polynomial coefficients.

TR_Map_TT2: Used for inspection of 3-tone PSM with only HT/QZ and HT/CR pattern edges. TT2 remaps the HT/QZ boundary of the slug to optimize sensitivity on quartz patterns. Shifting, stretching, and shaping functions can be parametrically adjusted to control the profile of the remap on the HT/QZ boundary. Curve fitting procedures may then be used to extrapolate the remap over all TR space. For example three parabolic coefficients can be computed from three conditions. Remap curves can be fit to the HT/QZ slug boundary, with a second condition to produce a GOC remap on chrome, and a third condition to define the curvature.

TR_Map_TT3: Used for inspection of 3-tone PSM with all pattern edge combinations. There are three TT3 options or variations, depending on which two pattern edges are renormalized. One option remaps the HT/QZ and CR/QZ boundaries of the slug to optimize sensitivity on quartz pattern edges. A second TT3 option remaps the HT/CR and CR/QZ boundaries of the slug to optimize sensitivity on chrome pattern edges. A third TT3 option remaps the HT/CR and HT/QZ boundaries of the slug to optimize sensitivity on halftone pattern edges.

Shifting, stretching, and shaping functions can be parametrically adjusted to control the profiles on the two remapped boundaries. Curve fitting procedures may then be used to extrapolate the remap over all TR space. For example three parabolic coefficients can be computed from three conditions. Remap curves can be fit to the two remapped slug boundaries, with a third condition to define the curvature. Other functions and parameters may be necessary to define GOC domains. For example, one type of GOC remap varies linearly with T between two endpoints on the HT/CR slug boundary.

Figure 36:
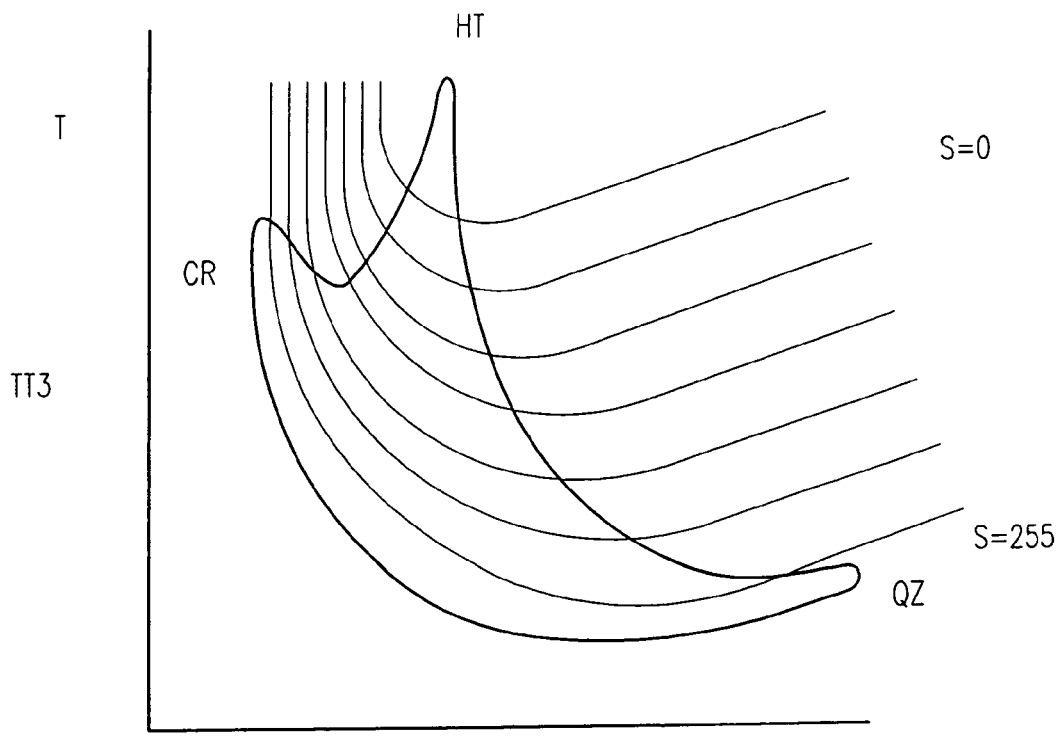
FIG. 36 illustrates the condition where TT3 renormalizes the HT/CR and HT/QZ slug boundaries.
Figure 37:
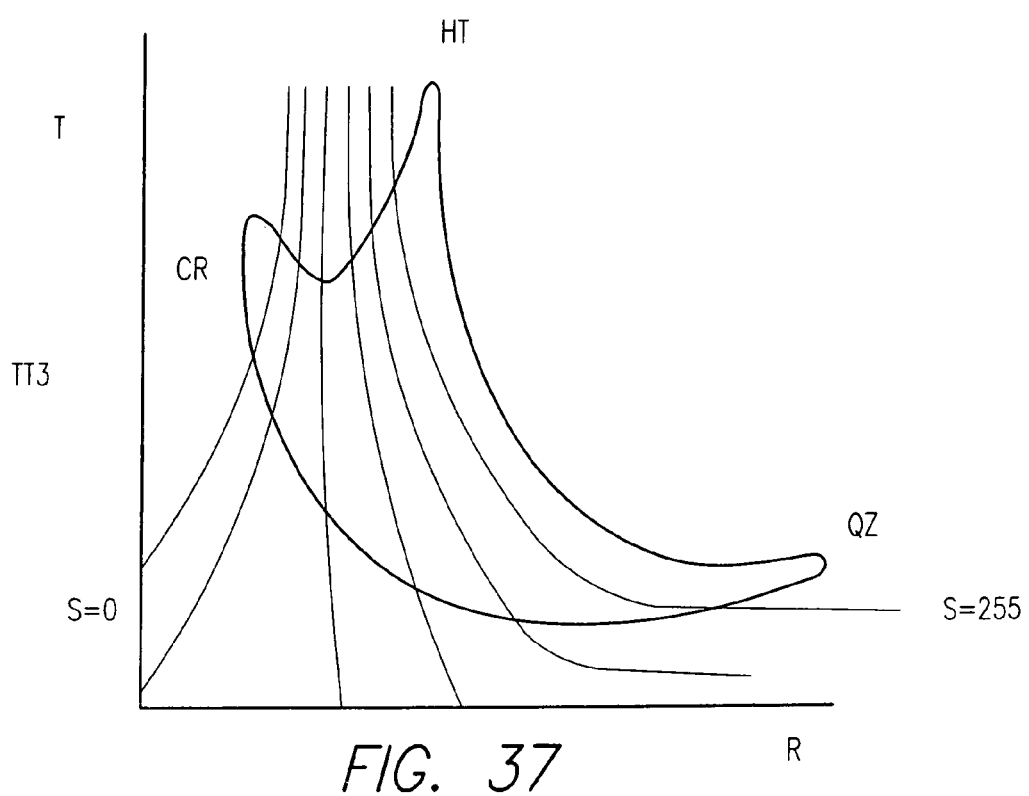
FIG. 37 shows the condition where TT3 renormalizes the HT/CR and CR/QZ slug boundaries.

FIGS. 31 through 35 illustrate the various TR Map species described above. These remap (S) contours have been graphed to exhibit the general dependence of each remap on T and R inputs. One TT3 example, illustrated in FIG. 34, has negative GOC slope, with respect to T. Another TT3 example, illustrated in FIG. 35, has positive GOC slope. An alternative to GOC for HT/CR inspection can be derived by fitting the S(T,R) polynomials to the HT/CR slug. FIGS. 36 and 37 illustrate two possible variations to this alternative TT3 approach. In FIG. 36, TT3 renormalizes the HT/CR and HT/QZ slug boundaries. In FIG. 37, TT3 renormalizes the HT/CR and CR/QZ slug boundaries. With these various TT3 options, the system can be set up for three-tone mask inspection with optimum sensitivity on any selected material. As shown in certain of FIGS. 31-37, the use of S=0 and S=255 constitute indicia representing stored elements of the remapped image, where the remapped image may be stored as a 256 element array.

TR_Map_T: Passes T and rejects R. Primarily for diagnostic purposes, although it can have useful applications including OPC (Optical Proximity Correction) inspection and second-level ADI.

TR_Map_R: Passes R and rejects T. Useful for ADI.

While the invention has been described in connection with specific embodiments thereof, it will be understood that the invention is capable of further modifications. This application is intended to cover any variations, uses or adaptations of the invention following, in general, the principles of the invention, and including such departures from the present disclosure as come within known and customary practice within the art to which the invention pertains.

What is claimed is:

1. A method for inspecting a specimen performed using an inspection system comprising a computing device, the method comprising:
    classifying types of specimens having characteristics and defects into at least one species;
    performing a transmitted energy inspection and a reflected energy inspection of said specimen, thereby producing a transmitted representation and a reflected representation of said specimen; and
    modifying at least one of the transmitted representation and the reflected representation by adjusting a boundary of at least one of the transmitted representation and reflected representation based on characteristics of the species associated with the specimen.

2. The method of claim 1, wherein said modifying utilizes a transmitted-reflected look up table having coefficients based upon known characteristics of previously inspected specimens.

3. The method of claim 2, wherein boundaries of said specimen are remapped to optimize sensitivity on edges having predetermined compositions.

4. The method of claim 1, further comprising applying shifting, stretching, and shaping functions to at least one of the transmitted representation and the reflected representation.

5. The method of claim 1, further comprising normalizing at least one of said transmitted representation and said reflected representation.

6. The method of claim 1, further comprising applying curve fitting to at least one of said transmitted representation and said reflected representation.

7. The method of claim 1, further comprising selectively ignoring at least one of the transmitted representation and the reflected representation.

8. A method for inspecting a specimen having at least one feature located thereon performed using an inspection system employing a computing device, the method comprising:
    performing a transmitted energy inspection and a reflected energy inspection of said specimen;
    submitting results from said transmitted energy inspection and said reflected energy inspection to a transmitted-reflected look up table, wherein said transmitted-reflected look up table comprises transmitted and reflected modification parameters dependent upon predetermined characteristics of said at least one feature, thereby determining modified results; and
    outputting modified combined transmitted energy data and reflected energy data modified based on the modified results determined by said transmitted-reflected look up table.

9. The method of claim 8, wherein boundaries of said specimen are remapped to optimize sensitivity on edges located on said specimen having predetermined compositions.

10. The method of claim 8, wherein said submitting results in a transmitted representation and a reflected representation, further comprising applying shifting, stretching, and shaping functions to at least one of the transmitted representation and the reflected representation.

11. The method of claim 8, wherein said submitting results in a transmitted representation and a reflected representation, further comprising normalizing at least one of said transmitted representation and said reflected representation.

12. The method of claim 8, wherein said submitting results in a transmitted representation and a reflected representation, further comprising applying curve fitting to at least one of said transmitted representation and said reflected representation.

13. The method of claim 8, wherein said submitting results in a transmitted representation and a reflected representation, further comprising selectively ignoring at least one of the transmitted representation and the reflected representation.

14. A method for inspecting a specimen performed using an inspection system employing computing device, the method comprising:
    performing a light calibration function comprising capturing transmitted and reflected images and quantifying extreme values for transmitted and reflected images;
    performing a transmitted-reflected map calibration function on the specimen, producing a transmitted-reflected map function;
    loading the transmitted-reflected map function into a lookup table, producing a set of inspection parameters; and
    inspecting the specimen based on the inspection parameters.

15. The method of claim 14, further comprising modifying said transmitted representation and said reflected representation using a transmitted-reflected (TR) map function having functionality based on specimen inspection sensitivities for species of specimens having characteristics similar to those of the specimen prior to said inspecting.

16. The method of claim 15, wherein boundaries of said specimen are remapped to optimize sensitivity on edges having predetermined compositions.

17. The method of claim 14, further comprising applying shifting, stretching, and shaping functions to at least one of the transmitted representation and the reflected representation.

18. The method of claim 14, further comprising normalizing at least one of said transmitted representation and said reflected representation.

19. The method of claim 14, further comprising applying curve fitting to at least one of said transmitted representation and said reflected representation.

20. The method of claim 14, further comprising selectively ignoring at least one of the transmitted representation and the reflected representation.

* * * * *

UNITED STATES PATENT AND TRADEMARK OFFICE
CERTIFICATE OF CORRECTION

PATENT NO. : 7,664,310 B2 Page 1 of 1
APPLICATION NO. : 11/023136
DATED : February 16, 2010
INVENTOR(S) : David G. Emery It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1384 days.

Signed and Sealed this

Thirtieth Day of November, 2010

David J. Kappos
*Director of the United States Patent and Trademark Office*